(12) United States Patent
Kuhry et al.

(10) Patent No.: US 9,663,864 B2
(45) Date of Patent: *May 30, 2017

(54) BIOLOGICAL/ELECTROLYTIC CONVERSION OF BIOMASS TO HYDROCARBONS

(71) Applicants: Ion Research, Inc., Skokie, IL (US); The United States of America, as Represented by the Secretary of Agriculture, Washington, DC (US)

(72) Inventors: Anthony B. Kuhry, Skokie, IL (US); Paul J. Weimer, Madison, WI (US)

(73) Assignees: The United States of America, as Represented by the Secretary of Agriculture, Washington, DC (US); ION Research, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,971

(22) Filed: Aug. 20, 2014

(65) Prior Publication Data
US 2014/0353163 A1 Dec. 4, 2014

Related U.S. Application Data

(63) Continuation of application No. 13/954,294, filed on Jul. 30, 2013, now abandoned, which is a continuation of application No. 12/760,911, filed on Apr. 15, 2010, now Pat. No. 8,518,680.

(51) Int. Cl.
| | | |
|---|---|---|
| C12P 7/64 | (2006.01) |
| C12P 5/00 | (2006.01) |
| C12N 1/22 | (2006.01) |
| C25B 3/04 | (2006.01) |
| C12P 3/00 | (2006.01) |
| C12P 5/02 | (2006.01) |
| C12P 7/40 | (2006.01) |
| C12P 7/52 | (2006.01) |
| C12P 7/54 | (2006.01) |
| C12P 39/00 | (2006.01) |
| C25B 1/02 | (2006.01) |

(52) U.S. Cl.
CPC ............... *C25B 3/04* (2013.01); *C12N 1/22* (2013.01); *C12P 3/00* (2013.01); *C12P 5/02* (2013.01); *C12P 5/023* (2013.01); *C12P 5/026* (2013.01); *C12P 7/40* (2013.01); *C12P 7/52* (2013.01); *C12P 7/54* (2013.01); *C12P 7/6409* (2013.01); *C12P 39/00* (2013.01); *C25B 1/02* (2013.01); *Y02E 50/343* (2013.01)

(58) Field of Classification Search
CPC .... C12P 7/54; C12P 7/40; C12P 39/00; C12N 1/20; Y02E 50/10; Y02E 50/343
USPC ................................................ 535/140, 161
See application file for complete search history.

(56) References Cited

U.S. PATENT DOCUMENTS

| | | | | |
|---|---|---|---|---|
| 5,504,004 A * | 4/1996 | Guettler | ............... | C12R 1/01 435/145 |
| 8,518,680 B2 * | 8/2013 | Kuhry | ............... | C12N 1/22 435/166 |

OTHER PUBLICATIONS

Hu et al. Process Biochem 2005, 40, pp. 2371-2377.*
Hivaisi et al. Biomass Bioenrg 1995, 8, pp. 45-50.*

* cited by examiner

*Primary Examiner* — Robert Mondesi
*Assistant Examiner* — M D. Younus Meah
(74) *Attorney, Agent, or Firm* — John D. Fado; G. Byron Stover

(57) ABSTRACT

Hydrocarbon and hydrogen fuels and other products may be produced by a process employing a combination of fermentation and electrochemical stages. In the process, a biomass contained within a fermentation medium is fermented with an inoculum comprising a mixed culture of microorganisms derived the rumen contents of a rumen-containing animal. This inoculated medium is incubated under anaerobic conditions and for a sufficient time to produce volatile fatty acids. The resultant volatile fatty acids are then subjected to electrolysis under conditions effective to convert said volatile fatty acids to hydrocarbons and hydrogen simultaneously. The process can convert a wide range of biomass materials to a wide range of volatile fatty acid chain lengths and can convert these into a wide range of biobased fuels and biobased products.

78 Claims, 1 Drawing Sheet

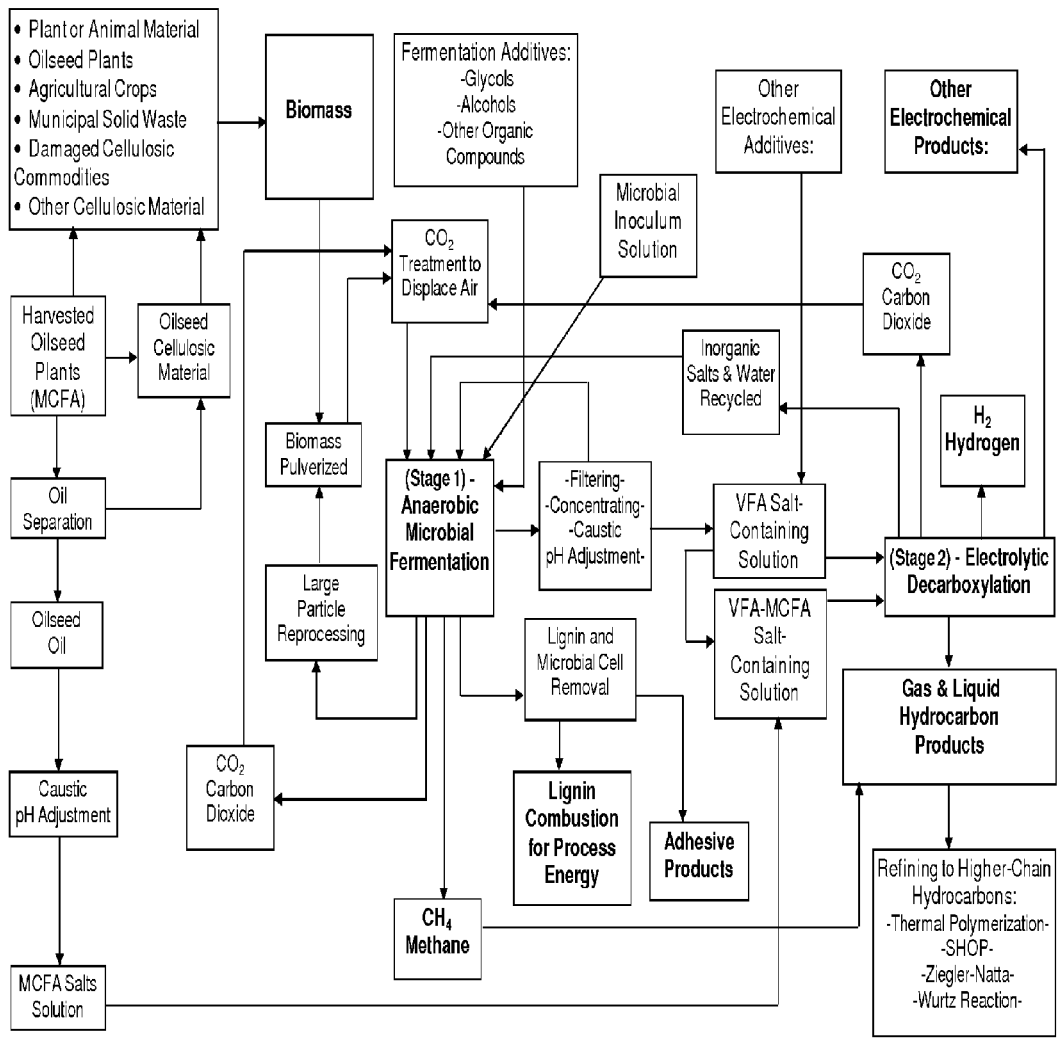

BIOLOGICAL/ELECTROLYTIC CONVERSION OF BIOMASS TO HYDROCARBONS

This is a continuation of application Ser. No. 13/954,294 filed 30 Jul. 2013, now ABN, which is a continuation of application Ser. No. 12/760,911 filed 15 Apr. 2010, now U.S. Pat. No. 8,518,680 which claims priority from provisional application No. 61/212,949 filed 17 Apr. 2009, all of which are herein incorporated by reference in their entirety.

BACKGROUND OF THE INVENTION

Field of the Invention

The invention is drawn to a novel method to produce hydrocarbon and hydrogen fuels simultaneously from biomass by a combination of fermentation and electrolysis.

Description of the Prior Art

The essential role of renewable fuels in fostering economically and environmentally sustainable growth is now widely recognized. Although technologies for providing electricity via wind, hydropower, and direct biomass consumption are widely employed, the production of liquid transportation fuels remains the greatest energy security issue in the U.S. today. Corn ethanol, once touted as a major future source of motor fuels, has succeeded in the marketplace only through substantial government subsidies to producers, and questions regarding its environmental sustainability, net energy balance, and role in exacerbating food shortages have now come to the fore.

Cellulosic ethanol is considered to be a more promising long-term source of transportation fuels (Lynd et al., 2002). Cellulosic materials are available in much larger quantities; can be produced on more marginal lands; feature a much larger net energy balance; and do not have a competing human food use. However, despite major funding efforts, development of economically viable cellulosic ethanol technologies have not yet attained commercial success. Chemical pretreatment is considered necessary to enhance the accessibility of the feedstock to enzymatic attack, yet such pretreatment adds costs, generates a waste stream, and produces certain chemical products that inhibit sugar fermentation. Contaminating microbes such as lactic acid bacteria can convert considerable amounts of the hydrolyzed sugars to products other than ethanol, necessitating expensive control measures to permit maintenance of the fermentative monoculture; this is already a major problem in the corn ethanol industry, which has become one of the major users of antibiotics in the U.S. (Olmstead, 2009). Moreover, the most active of the ethanol producers ferment only the hexose fraction of carbohydrate, and even the best strains that utilize the pentose sugar fraction only ferment the carbohydrate fraction but not the other components (proteins, nucleic acids, lipids, organic acids and other phytochemicals) that represent a substantial proportion of plant biomass. This greatly reduces the yield of fuel product. Finally, no obvious use has emerged for the unfermented residue—a critical shortcoming given its likely large volume and the likely low profitability of the cellulosic ethanol process.

Ethanol has a relatively low energy density (with attendant reductions in vehicle miles-per-gallon), and for most gasoline-powered vehicles can only be blended to a low proportion of the total fuel mixture. These disadvantages, along with the slow pace of development of cellulosic ethanol technology, have stimulated a search for routes to convert biomass to hydrocarbon fuels (Regalbuto, 2009).

Several such schemes have been proposed. Some of these rely on chemical conversion of biomass materials under heat and pressure (often in the presence of expensive catalysts) and yield either liquids (e.g., pyrolytic oils) or gases that can be reformulated into liquid motor fuels. Several biologically based processes have also been proposed. These processes face some formidable hurdles. For example, photosynthetic algal-based processes either require large areas for cultivation (because of the shallow depth of the photic layer under intense cultivation, while the "dark algal" process or processes based on bacteria that have been genetically engineered for hydrocarbon biosynthesis require sugars as the feedstock (which revisits the high cost of cellulolytic enzymes that has hampered ethanol production via simultaneous saccharification and fermentation).

Biorefinery Processes:

Biorefinery processes that produce various types of biobased fuels from biomass are well known. It is known, for example, that natural mixtures of anaerobic microbial cultures that work together to digest biomass material occur in habitats such as the rumen of ruminant animals, sewage sludge, soil, landfills, aquatic (freshwater, marine, and brackish) sediments, and insect (e.g., termite) guts. These mixed microbial cultures work in concert to provide the necessary enzymes to convert biomass into organic acids. The organic acids are primarily "Volatile Fatty Acids" (VFA) which includes straight and branched chain fatty acids with carbon chain lengths from C2 to C6.

As a result of thousands of years of natural evolution of biomass processing, the ruminal fermentation is a particularly attractive process because it is natural, rapid, and efficient (Hungate, 1950, 1966); it converts most biomass components to useable products (Weimer et al., 2009); and it can readily be conducted in a biorefinery (i.e., in vitro in bioreactors; Goering and Van Soest, 1970).

Ruminal microbes have long been known to convert cellulosic and other feed materials to VFA (Hungate, 1950, 1966), and have also been used for treating organic wastes. In the RUDAD (Rumen-Derived Anaerobic Digestion) process (Zwart et al., 1988), mixed ruminal microbes (including both bacteria and protozoa) are used in a primary stage fermentation to convert cellulosic and other organic wastes to VFA that are passed to a second reactor in which the VFA are converted by other microorganisms to methane and carbon dioxide. The process is used exclusively for waste treatment, although as in many other wastewater treatment plants, the methane produced can be used as a fuel to offset the operating energy requirement of the treatment plant. Differences in the growth rates of microbes in the two reactors, along with problems in maintaining flocculation in the bioreactors, have limited the utility of the RUDAD process (Hack and Vellinga, 1995). An improved process (described in Hack and Vellinga, 1995, U.S. Pat. No. 5,431,819) employs a three-stage process in which the solids fraction from the primary cellulosic fermentation is further degraded in another reactor while the liquid phase from the primary fermentation is further treated in a third, methanogenic, reactor.

Biorefinery-produced organic acids may be converted into useful fuels by different methods (e.g., those of Holtzapple and of Bradin). Holtzapple et al. (1999) describe processes that produce biofuels of mixed alcohols (Mix-Alco) and other products such as mixed ketones, by thermochemical treatment of organic acids that are produced by the action of natural microbial mixtures on biomass material. These processes are described in detail in U.S. Pat. Nos. 5,693,296; 5,865,898; 5,874,263; 5,962,307; 5,986,133;

5,969,189; 6,043,392; 6,262,313; 6,395,926, and U.S. Pat. No. 6,478,965. The natural mixed microbial cultures used by Holtzapple are obtained primarily from anaerobic sewage digesters comprising municipal solid waste (MSW) and sewage sludge (SS) that transform chemically pretreated biomass material into volatile fatty acid (VFA) mixtures as described in U.S. Pat. No. 6,043,392 under the "Pretreatment and Fermentation" section. The biomass components that are converted into organic acids are: cellulose, hemicellulose, pectin, sugar, protein, and fats. These processes are characterized by alkaline pretreatment of biomass, followed by the fermentation process, followed by dewatering, thermal conversion to produce ketones, and addition of hydrogen plus catalyst, heat, and pressure, all of which are needed to produce mixed alcohol fuel products. Total reaction processing times are therefore, necessarily long. In order to facilitate VFA accumulation during the fermentation stage, Holtzapple's process typically uses a "stuck" fermentation, in which microbial methane formation is prevented by keeping the pH low and/or by adding specific (toxic) inhibitors of methanogenesis (e.g., bromoform [$CHBr_3$], or iodoform [$CHI_3$]). This causes the fermentation intermediates (organic acids) to accumulate, but also leaves these toxic inhibitors of methanogenesis in the wastewater stream necessitating further cleanup.

Biofuels can also be produced by using specific types of microbes, as opposed to mixed microbial cultures, in order to produce specific types of hydrocarbons exclusively from sugars. For example, Bradin (2007; publication WO 2007/095215 A2) describes a process that produces n-hexane from the fermentation of sugars, using specific natural bacteria or yeast that produce specifically butyric acid as a single product. The butyric acid is then subjected to Kolbe dimerization electrolysis to form n-hexane. However, the preferred microbes are selected to reduce or eliminate acetic acid as a byproduct because it lowers butyric acid yield. Moreover, the preferred microbes must be either naturally isolated or genetically engineered pure cultures, and must be cultivated under controlled conditions to prevent culture contamination, thus reducing flexibility and increasing the cost. In addition, in order to produce sugars from complex carbohydrates such as cellulose and hemicellulose, specific enzymes must be added to the biomass, thus further adding to the reaction processing time and the cost. The Bradin process also requires the separation of lignin from cellulose and hemicellulose, by other enzymes or oxidizing agents to delignify the biomass prior to fermentation. The single n-hexane product also requires further refinement in order to be used as a transportation fuel.

Anaerobic fermentations of plant biomass yield a variety of fermentation end products having high potential energy. Some of these products, like ethanol or butanol, can be recovered by distillation and used directly as motor vehicle fuels. Others, like VFA (e.g., acetic, propionic or butyric acids) can be produced in substantial quantities, but are not directly usable as fuels.

The literature contains a number of examples of conversions of carboxylic acids to hydrocarbons using electrochemistry. For example, the alkyl groups of fatty acids can be combined tail-to-tail during anodic electrolytic decarboxylation to yield alkanes (e.g., ethane from acetic acid, butane from propionic acid, etc.), the so-called Kolbe reaction. The Kolbe reaction can proceed via dimerization of similar radical species to produce single alkanes, or cross-radical reactions with dissimilar radical species to produce alkane mixtures (see Table 1). Moreover, fatty acids can be partially cleaved and converted to alkenes (e.g., ethylene from propionic acid) by the so-called Hofer-Moest reaction. The Hofer-Moest reaction can produce alkenes via deprotonation and alcohols via substitution. Under certain reaction conditions, dienes and trienes can also be produced. The hydrocarbon reaction formulas are shown in Formula 1, comparing one-electron (Kolbe) and two-electron (Hofer-Moest) schemes for electrolytic decarboxylation (Adapted from Lund [2001] and Seebach et al. [1995]).

Formula 1

Kolbe and Hofer-Moest Reactions

I. Kolbe Electrochemical Decarboxylative Radical Coupling (Dimerization)=Single Alkanes:

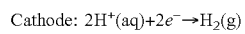

II. Kolbe Electrochemical Decarboxylative Cross-Radical Coupling=Alkane Mixtures:

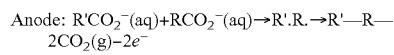

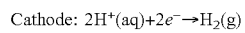

III. Hofer-Moest Electrochemical Oxidative Decarboxylation (Deprotonation)=Alkenes:

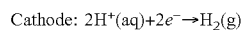

The Kolbe and Hofer-Moest reactions are among the oldest reactions described in electrochemistry. Although they can readily convert VFA to alkanes and alkenes (or alcohols and esters), they have generally been used commercially in synthesis of low-volume specialty chemicals. Electrochemical Conversion of Fatty Acids to Alkanes from Biomass:

As a result of petroleum price increases due to increased demand, many processes for alternatives to petroleum liquid fuels were developed in the 1970's in the U.S. and other countries. Most of the emphasis has been on ethanol production, and little was devoted to the production of renewable liquid alkane hydrocarbon fuels. Alkane liquid fuels research was performed in the late 1970's concerning the feasibility of Kolbe electrolysis of mixed bacterial anaerobic fermentations using inocula from sewage sludge (Levy et. al., 1983). The research disclosed that these microorganisms converted specifically the sugar portion (hexose and pentose sugars) from both cellulose and hemicellulose to organic acids. The fermentation produced variable amounts of C2 to C6 carbon chain VFA including acetic, propionic, butyric, valeric, and caproic acids. These carboxylic acids were produced by nonsterile anaerobic fermentations. The higher chain VFA (butyric, valeric and caproic acids) were separated and concentrated by liquid-liquid extraction with kerosene. It was theorized that the higher chain VFA could be treated by electrolytic oxidation (Kolbe and Hofer-Moest electrolysis) to produce hydrocarbons, alcohols, and esters. The lower chain VFA (acetic, propionic) remained in the primary fermenter as a feedstock in order to produce higher chain VFA in subsequent primary fermentations. This fermentation using sewage sludge at long residence times (at least 5 to 18 days or longer) necessitated the suppression of the methane-forming microorganisms (methanogens) by the use of a chemical inhibitor (viz. BES, 2-bromoethane sulfonic acid) similar to the Holtzapple process mentioned above. Thus, despite these advances, the need remains for improved techniques for producing hydrocarbon fuels from renewable resources.

SUMMARY OF THE INVENTION

We have now discovered a novel process for producing hydrocarbon fuels and other products by a process employing a combination of fermentation and electrochemical stages (referred to as herein as Biological-Electrolytic Conversion, or BEC). In this process, a biomass-containing fermentation medium is fermented with a mixed culture of microorganisms derived the rumen contents of a ruminant animal, and incubated under anaerobic conditions and for a sufficient time to produce volatile fatty acids. The resultant volatile fatty acids (VFA) are then subjected to electrolysis under conditions effective to convert them to gaseous and liquid hydrocarbons and hydrogen gas ($H_2$), with carbon dioxide ($CO_2$) as a co-product. The process of this invention can produce a wide range of VFA chain lengths and can convert each of these into biobased fuels and biobased products.

The process uses the primary ruminal fermentation, in vitro, for a rapid, high-yield conversion, and can also use an optional secondary fermentation with an augmented microbial inoculum to convert lower chain volatile fatty acids to higher chain volatile fatty acids, if desired. An additional separate fermentation can be used to convert carbon dioxide ($CO_2$) and hydrogen ($H_2$) produced from the in vitro ruminal fermentation and the electrolysis stages, respectively, into acetic acid, which can then be included as a feedstock in a subsequent electrolysis stage. Alternatively, this carbon dioxide ($CO_2$) and hydrogen ($H_2$) can be converted in a separate bioreactor to methane gas. This increases the overall yield of the fuel products, and utilizes carbon dioxide ($CO_2$) as a fuel-producing feedstock instead of generating a waste product. Thus, as an industrial process, BEC can convert virtually any type of biomass into a variety of hydrocarbon fuels and hydrogen gas ($H_2$) without the high temperatures or high energy requirements that are inherent in some other conversion methods, such as pyrolysis.

In accordance with this discovery, it is an object of this invention to provide a rapid, flexible, inexpensive, and efficient process for the production of hydrocarbon and hydrogen fuels from biomass.

Another object of this invention is to provide a process that uses mixed cultures from ruminal inocula to produce volatile fatty acids from biomass in a single-stage bioreactor, which volatile fatty acids may then be converted into a plurality of hydrocarbon products and hydrogen gas ($H_2$) in a second reactor using a non-biological process employing electrochemistry.

Another object of this invention is to provide a process for converting mixtures of organic acids produced by microbial anaerobic fermentation of biomass into a variety of gaseous and liquid hydrocarbon fuels, hydrogen and other chemical products, via electrolytic decarboxylation.

Another object of this invention is to provide a process for combining organic acids obtained by anaerobic fermentation of biomass with other organic acids already present in plant or animal biomass material, and converting these combined organic acid mixtures into a variety of useful hydrocarbon fuels, hydrogen and other chemical products, via electrolytic decarboxylation.

Another object of this invention is to provide a process for combining organic acids obtained by anaerobic fermentation of biomass with other industrial organic chemicals and converting these combined organic mixtures into a variety of useful hydrocarbon fuels, hydrogen and other chemical products, via electrolytic decarboxylation.

Another object of this invention is to provide a process that will offer a solution to the ever-growing environmental problem of landfilling cellulosic biomass waste, by economically converting this waste into hydrocarbon fuels, hydrogen and other chemical products, eliminating the need for landfilling of this material.

Another object of this invention is to provide a process that will offer an economic solution to biomass waste disposal by utilizing damaged, spoiled, or spent cellulosic commodities to produce hydrocarbon fuels, hydrogen and other chemical products by reprocessing them instead of discarding in landfills.

Other objects and advantages of this invention will become readily apparent from the ensuing description.

BRIEF DESCRIPTION OF THE DRAWINGS

FIG. 1 shows a flow diagram describing a preferred embodiment of the invention for producing hydrocarbon fuels, hydrogen, and other biobased products from biomass.

DEFINITIONS

The following terms are employed herein:

Biomass can be any plant or animal material containing carbohydrate (including cellulose, hemicelluloses, starch, pectins, and fructans), protein, nucleic acid, organic acid, or fat. The term biomass refers to any organic matter that is available on a renewable or recurring basis, such as, but not limited to agricultural crops and trees, wood and wood wastes and residues, plants (including aquatic plants), grasses, residues, fibers, and animal wastes, food wastes, municipal wastes, and other waste materials.

The term biobased fuel or biofuel refers to any transportation fuel produced from biomass.

The term biobased product refers to an industrial product (including chemicals, materials, and polymers) produced from biomass, or a commercial or industrial product (including animal feed and electric power) derived in connection with the conversion of biomass to fuel.

Hydrocarbon biobased fuels consist exclusively of carbon and hydrogen, such as alkanes, alkenes, dienes, and trienes. Other chemical biobased products include carbon and hydrogen components combined with other chemical elements such as oxygen, nitrogen, etc.

The term Biological-Electrolytic Conversion or "BEC" is used herein to describe the process of the invention disclosed herein. The BEC is a biorefinery process that converts biomass into biobased fuels and biobased products.

The conversion of biomass into organic acids refers to the conversion to volatile fatty acids (VFA), which includes straight and branched chain fatty acids with carbon chain lengths from C2 to C6, including but not limited to acetic, propionic, butyric, isobutyric, 2-methyl butyric, valeric, isovaleric, and caproic acids. Medium Chain Fatty Acids (MCFAs) and Long Chain Fatty Acids (LCFAs) are naturally produced from certain plant and animal products and together span the range of carbon chain lengths from C8 to C22. This invention describes a process that converts VFA, by itself, into biobased fuels and biobased products. Additionally, this invention describes a process that converts combinations of both VFA and VFA/MCFA/LCFA into many different biobased fuels and biobased products (see Table 1). As used herein, MCFA refers to both MCFA and LCFA.

DETAILED DESCRIPTION OF THE INVENTION

The preferred inoculum for use herein in the fermentation to produce the volatile fatty acids from biomass is a mixed culture of microorganisms derived from the rumen contents of a rumen-containing (ruminant) animal. We have discovered that the use of a ruminal inoculum significantly reduces the length of the fermentation and increases yields in comparison to inocula prepared from other sources such as sewage sludge. Moreover, use of the ruminal inoculum also eliminates the need to suppress methane production during the primary fermentation with chemical inhibitors; the primary fermentation using ruminal inocula to produce volatile fatty acids from biomass as described in this invention is preferably conducted without the addition of methane production inhibitors. The time course for the ruminal fermentation without methanogenic inhibitors is typically 2-3 days, as opposed to 5 to 20 days or longer for anaerobic digestion with sewage sludge inocula and methanogenic inhibitors. The fermentation time course is affected by biomass loading where higher concentrations of biomass solids require longer residence times. As a comparison, fermentation time course for human and animal sewage conversion to methane without inhibitors normally takes about 3 weeks. Another measure of the fermentation time course is the first-order rate constant (k) for conversion of particular biomass components:

|  | Rumen | Sewage Sludge |
|---|---|---|
| k for cellulose | 0.06-0.1/hr$^a$ | 0.09/day (0.0038/hr)$^c$ |
| k for starch | 0.384/hr$^b$ | 0.34/day (0.014/hr)$^c$ |

$^a$Weimer, et al., 1990.
$^b$Weimer and Abrams, 2001.
$^c$Levy et al., 1983.

The use of the ruminal inocula provides other advantages as well. The microorganisms of this mixed culture produce their own enzymes for hydrolyzing and fermenting complex substrates such as cellulose, hemicelluloses, pectins, starches, sugars, proteins, nucleic acids, and dicarboxylic and tricarboxylic acids to the high-energy end product volatile fatty acids. Thus, the biomass substrate does not need to be chemically or enzymatically hydrolyzed to low molecular weight sugars prior to the fermentation, and minimal additional nutrients are used. Furthermore, unlike processes using other inocula, the ruminal inoculum produces volatile fatty acids rather than ethanol or methane as the primary fermentation products. The microorganisms of the ruminal inoculum also convert not only the carbohydrate (hexoses, pentoses, and their polysaccharides) portion of the biomass, but also the protein, nucleic acid, dicarboxylic and tricarboxylic acid fractions, and some of the lipid fraction to volatile fatty acids. Therefore, yields of volatile fatty acids from these mixed culture fermentations are much higher than in conventional biomass fermentations employing carbohydrate-fermenting microbes. The protein fermentation by the rumen-derived mixed culture is particularly beneficial, in that some of the volatile fatty acids produced (in addition to acetic, propionic, butyric and valeric acids) include 2-methylpropionic (isobutyric), 2-methylbutyric, and 3-methylbutyric (isovaleric) acids. These branched-chain volatile fatty acids, upon subsequent electrolytic conversion, will yield branched-chain hydrocarbons that may have improved fuel performance properties.

The ruminal inoculum for use herein may be obtained from any ruminant animal, although caprine (goat), ovine (sheep) and bovine (cattle) species are preferred, and bovine is particularly preferred. The ruminal contents, primarily liquid although solids may be included, can be collected from the ruminant animal through an implanted rumen fistula, or through stomach tube, ruminocentesis, or directly from rumen contents at slaughter. Once collected the ruminal contents may be used directly as the inoculum in the fermentation herein. However, in a preferred embodiment, the mixed populations of microorganisms in the contents are first subjected to one or a plurality of successive, small-scale anaerobic fermentations with the desired biomass substrate prior to their use in a larger-scale fermentation. This adaptation of the rumen microorganisms increases their tolerance to the volatile fatty acids, and increases the molar concentration of volatile fatty acids in the fermentation. Although the rumen contents used herein contain a diverse mixed population of microorganisms, the microbial consortia are relatively stable in culture, and can be maintained by sequential transfer without sterilization of the substrate or reactor vessels. The ruminal inocula from these enrichment cultures are also essentially devoid of the protozoa that reduce the overall efficiency of the fermentation by consuming the fermentative bacteria.

An undefined, mixed, bacterial composition of a preferred adapted ruminal inoculum of this invention, designated RCBP, has been deposited under the provisions of the Budapest Treaty in the Agricultural Research Service Culture Collection in Peoria, Ill., on May 6, 2010, and has been assigned deposit accession number NRRL B-50366. The composition is composed of an undefined, yet stable mixture of anaerobic bacteria.

The ruminal inoculum may be used alone or optionally may be augmented by addition of one or more supplemental pure or mixed cultures of microorganisms. Anaerobic fermentation of biomass with the microorganisms of the ruminal inoculum produce primarily lower chain volatile fatty acids (i.e., propionic and acetic with relatively less butyric and isobutyric) with low amounts of higher chain C5 and C6 volatile fatty acids (valeric and caproic). However, addition of supplemental inocula can increase the production of the C4, C5, and C6 higher chain volatile fatty acids. As an alternative to adding supplemental microorganisms to the primary fermentation of the biomass with the ruminal inoculum, these supplemental microorganisms may be used as the inocula for a secondary fermentation of the biomass, following the primary fermentation with the ruminal inoculum. For instance, an additional, separate fermentation can be used to convert carbon dioxide ($CO_2$) and hydrogen ($H_2$) produced from the ruminant inoculum fermentation and the electrolysis stages, respectively, into acetate, which can then be included as a feedstock in a subsequent electrolysis stage. Alternatively, this carbon dioxide ($CO_2$) and hydrogen ($H_2$) can be converted in a separate fermentation to methane gas for use as a fuel. Without being limited thereto, examples of supplemental microorganisms include one or more of the following: *Clostridium kluyveri*, *Clostridium butyricum*, *Clostridium tyrobutyricurn*, *Butyrvibrio fibrisolvens*, mixed culture of microorganisms derived from sewage sludge, landfills, soil or aquatic (freshwater, marine, brackish) environments, or mixed cultures of microorganisms derived from the gut of termites or other insects. Supplementation with the butyric acid producing *B. fibrisolvens* is preferred, particularly as an augment with the ruminant inoculum in the primary fermentation. *B. fibrisolvens* is capable of utilizing hemicelluloses, and it is envisioned that its use should increase the production of butyric acid. Due to its relatively slow growth rate, *C. kluyveri* is preferably employed in a secondary fermentation after the ruminant inoculum fermentation. While the organism produces butyric and caproic acids, a suitable electron donor such as ethanol (Kenealy et al., 1995), or hydrogen gas ($H_2$) (Kenealy and Waselefsky, 1985), can be added to this secondary fermentation to increase the yield of the longer chain VFA (Kenealy et al., 1995). The hydrogen gas ($H_2$) can be supplied as the hydrogen produced by the cathodic reaction in the BEC electrolytic stage.

The production of the volatile fatty acids may be effected by fermentation of the biomass with the aforementioned ruminal inoculum in an aqueous medium, using conventional fermentation techniques under anaerobic conditions. Use of a $CO_2$ atmosphere is preferred, although it is envisioned that other gases such as $N_2$ may be used. Suitable pH and temperature ranges of the fermentation may typically range between about 4.5 to 7.5 and 30 to 50° C., respectively, with a pH and temperature between about 5.5 to 7.0 and 35 to 45° C., respectively, being preferred. The fermentation may be conducted as a batch, fed-batch or continuous process, in a single- or multi-stage reactor. The fermentation does not require, and is preferably conducted in the absence of, aseptic conditions, without sterilization of the biomass substrate, reactor, or any other components. The fermentation is incubated for a sufficient time to produce volatile fatty acids therein. The precise incubation period for the fermentation may vary somewhat with the biomass substrate and conditions, but the fermentation may be discontinued after about 1 to 4 days, preferably after 2 to 3 days, as the time for completion of the ruminal fermentation is typically 2 to 3 days. Depending upon the particular biomass used, volatile fatty acid concentrations in the fermentation broth from about 0.1M to 0.2 M, up to about 0.3 M, can be obtained by the fermentation process herein. As noted hereinabove, the primary fermentation is preferably conducted without the addition of an effective amount of methane production inhibitors (inhibitors of methanogenesis or methanogenic microorganisms), such as, but not limited to 2-bromoethane sulfonic acid (BES).

A variety of biomass substrates are suitable for use herein, including plants or parts, residue or waste material thereof. Without being limited thereto, biomass sources include agricultural crops (including fruits and vegetables), trees, forages, grasses, aquatic plants, bagasse, corn stover, corn cobs, hay, flax straw, oat hulls, wood (including timber, forestry slash, and other wood waste), sawdust, paper products, paper processing wastes (including fines from paper recycling), cardboard, and yard or landscape waste, spent sausage casings, mixed stands of vegetation, rotting, spoiled or devalued plant materials, and certain food processing wastes. Although cellulosic biomass substrates are preferred, animal wastes and waste products, including animal carcasses, may also be used. In an optional embodiment, the biomass fermentations may also include plant material (including plants or parts or materials thereof) that produce organic acids and/or medium chain fatty acids (MCFA) some of which are relatively inert to anaerobic degradation and do not need prior separation processing, which would carry through the fermentation, intact, to serve as precursors for liquid hydrocarbons such as octane and kerosene in the electrolysis stage.

Although the ruminal microorganisms readily ferment chemically or enzymatically pretreated feedstocks (that is, pretreatments which function to increase the availability of the fermentable substrates in the feedstock to the microorganisms, e.g., pretreatments with acid, base, oxidizing agents, or enzymes, and including but not limited to hydrolysis), no such chemical or enzymatic pretreatments are necessary in the process of the invention, and are preferably omitted. However, for large biomass materials, the materials should be reduced in size using conventional techniques such as simple mechanical grinding and/or rolling (e.g., burr milling). This physical pretreatment is preferred in order to decrease feedstock particle size, increase the aggregate surface area, and thus increase the fermentation rate. Any large feedstock particles that remain in the fermentation broth will settle out, and may be separated and re-ground, which mimics the characteristic chewing habits of ruminant animals (chewing the cud). In a preferred embodiment, a small amount of nutrients may be added to the fermentation medium to enhance microbial growth, with distillers dried grains (DDGs) or other low-cost nutrients being preferred. Other adjuvants which may be added to the fermentation include small amounts of caustic, such as NaOH, KOH or $Ca(OH)_2$ to produce salts of the volatile fatty acids and adjust pH. Other mineral salts may also be needed in small amounts to provide inorganic components of cell material, or osmotic balance for the microbial cells in the in vitro fermentation process.

In a particularly preferred embodiment, glycerol, a common byproduct of biodiesel production, may also be added to the biomass for fermentation by the ruminant inoculum. We have unexpectedly discovered that the addition of glycerol not only increases the production of propionic acid, but also increases the production of butyric acid during the fermentation. Other optional adjuvants include alcohols such as methanol, a common contaminant of the glycerol produced by biodiesel manufacture, and which is converted by the rumen microorganisms to a mixture of methane and $CO_2$ in a ratio of approximately 3:1. Yet other adjuvants which may be added include organic acids such as those naturally produced and available from natural sources. For example, fruits and fruit processing waste contain hydroxy-, dicarboxylic, and tricarboxylic acids such as malic acid and citric acid. These acids can be included in the process of the invention by addition of the fruit materials or separated acids to the fermentation medium, whereupon the hydroxy-, dicarboxylic, and tricarboxylic acids may be converted by fermentation to volatile fatty acids. Alternatively, the hydroxy-, dicarboxylic, and tricarboxylic acids from the fruit materials may be added after the anaerobic fermentation, directly to the volatile fatty acid salt containing solution, to obtain different electrolytic products.

As described above, the anaerobic fermentation of many biomass materials with the ruminant inoculum will typically produce C2 to C6 volatile fatty acids. In an optional yet preferred embodiment, the process may be modified by addition of one or more C8 to C22 MCFA, which will therefore produce even longer chain hydrocarbon products from the subsequent electrolysis, including octane and kerosene. Supplementation with MCFA may be effected by direct addition of MCFA, or by addition of materials incorporating MCFA such as materials from plants that produce MCFA, particularly oilseeds. In this embodiment, oilseed oils contain a variety of MCFA, are globally abundant, and may be obtained in large quantities. Common fatty acids available in large supply from various plant sources include, but are not limited to, coconut, palm kernel, *cuphea*, soybean, rapeseed, peanut, sunflower, and jatropha (see Tables 3, 4 and 5). Coconut oil, for example, contains a range of fatty acids with a characteristic profile that includes C8 to C18 carbon chain atoms. As with the organic acid containing fruit materials, these MCFA-containing plants or plant materials (e.g., seeds per se or the oil recovered from oilseeds) may be added to the anaerobic primary fermentation of the biomass materials by the ruminant inoculum. Most of the MCFA will pass through the fermentation unchanged, and the resulting mixtures of volatile fatty acids and MCFAs can then be pH-adjusted and subjected to the subsequent anodic electrolytic decarboxylation. Alternatively, the MCFA-containing plant materials may be processed separately from other biomass materials to recover the oilseed oils, which are converted to MCFA salts, and added to the volatile fatty acid-containing fermentation broth solution. The oilseed oils should first be treated with base (caustic pH adjustment) to make carboxylate salts, which can then be subjected to the anodic electrolytic decarboxylation. In accordance with this embodiment, a large variety of hydrocarbon products may then be produced on an industrial scale, limited only to the amount of feedstock.

In accordance with another alternative embodiment, by limiting the MCFA content of the fermentation broth to the lower carbon chain fatty acids (C8 to C10), liquid hydrocarbon products may be produced by electrolysis in relatively pure form. This can be readily performed by selecting specific fatty acid profiles from specific sources. For example, seed oil from certain species of *Cuphea* (e.g., *C. painteri, C. hookeriana*) may contain predominant amounts of C8 (caprylic acid) and C10 (capric acid); these two acids together can comprise up to 88%-93% of the total fatty acids in the oil (Table 4). Under Kolbe electrolysis conditions, C8 fatty acids react with VFA to produce liquid n-octane and higher carbon chain liquid hydrocarbons like kerosene (see Table 1). Many oilseed plants produce a large percentage of fatty acids in the C12-C18 range, which could be electrolytically converted with VFA into other higher kerosene-type fuels. Some oilseed plants produce even higher chain fatty acids and fats, for example, C20 (peanut oil, fish oil), C22 (rapeseed oil). The resulting hydrocarbons can be readily broken down into more desirable shorter chain alkanes with existing catalytic crackers. Combined with volatile fatty acid salt containing solutions, these new mixtures of organic acids (volatile fatty acid/MCFA) allow a large variety of hydrocarbon fuels and chemical products to be produced by cross-linking the radical intermediates through the anodic electrolytic decarboxylation process. Using this method, relatively pure liquid, as well as pure gas products can be produced directly, including high-quality transportation fuels such as n-octane or kerosene. These are all produced relatively pure without large quantities of contaminants such as nitrogen, sulfur, mercury, or particulates. Any traces of contaminating gases (ammonia, hydrogen sulfide) can be either recycled to the fermentation broth as nutrients for the microbes, or removed via adsorption to wood chips, or other adsorbent materials, or via reaction with iron or iron salts.

At the conclusion of the primary fermentation of the biomass with the ruminal inoculum, the volatile fatty acid mixtures from the fermentation broth typically yield an aqueous solution ratio of approximately 6:2:1 of acetic, propionic, and butyric acids at a total VFA concentration of about 0.1 M to 0.2 M within a pH range of about 5 to 6.5, although total volatile fatty acid concentrations up to 0.3 M may be produced. In one embodiment, the electrolysis of the volatile fatty acids to produce hydrocarbons may be performed directly upon the fermentation broth without further treatment or extraction of the volatile fatty acids therefrom. However, in a first preferred embodiment, the microbial cells, lignin-containing residues, and non-carboxylate anions (e.g., bicarbonates and carbonates) are removed from the broth (containing the carboxylate anions or salts of the VFA) prior to electrolysis. The cells, lignin-containing residues and non-carboxylate anions may be removed by one or more of a variety of techniques, such as filtration, flocculation, settling, centrifugation or precipitation. Soluble proteins may also be removed such as by an additional ultrafiltration step, as some dissolved proteins may decrease current flow to the anode and slow the electrolysis process when carried out in fermented broth. Non-carboxylate anions will also inhibit the electrolysis. In another preferred embodiment, the volatile fatty acids are also concentrated or extracted to a higher molar concentration or separated into individual volatile fatty acids, thereby improving yields or allowing the production of specific products. In a particularly preferred embodiment, the VFA are separated from the fermentation broth, and concentrated to improve electrolytic efficiency. The volatile fatty acids can be extracted efficiently by liquid-liquid extraction of the fermentation broth with alcohols such as butanol or isopropanol, or with other polar and non-polar organic solvents. Isopropanol can extract volatile fatty acids and is miscible with water, but is insoluble in highly saline solutions. Additions of salt (e.g., NaCl) to the aqueous fermented broth-isopropanol solution allow for an aqueous/alcohol separation layer to form, which can then be recovered. Alternatively, the volatile fatty acids may be concentrated by distillation, capacitive deionization (CDI), evaporation, ultrafiltration, reverse osmosis, forward osmosis, carbon nanotubes, or biomimetics. The recovered volatile fatty acid solution may also be sequestered stored and processed electrochemically at a later time.

Although filtering the fermentation broth is a useful method to improve electrolysis conditions within the fermented broths, concentrating the VFA from the fermentation broth is preferred because it eliminates or minimizes unwanted anodic electrolytic products. Concentrated organic acid substrates maximize the efficiency and effectiveness of the electrolytic process. It is envisioned and anticipated that the preferred electrolysis conditions include a concentrated carboxylate (VFA salts, VFA-MCFA salts) substrate solution relatively free of dissolved proteins and other unwanted anions. In this embodiment, the VFA are separated from the fermented broth and concentrated. This can be achieved by several known methods including distillation and liquid-liquid solvent extraction. Although VFA solvent extraction is the preferred concentration method over distillation due to cost considerations, other methods can be used that do not require heat or solvent processing that would otherwise increase the total BEC processing cost.

It is envisioned and anticipated that another concentration method will be preferred due to its low cost and effectiveness on an industrial scale. Capacitive Deionization (CDI) is an economical process that has been used for water purification and can be adapted to concentrate carboxylate (VFA salts, VFA-MCFA salts) anions within aqueous solutions. CDI uses very low voltages and very high surface area electrodes to electrostatically attract and hold anions and cations in aqueous solutions to their respective anode and cathode. High surface area electrodes can be any material but mainly include carbon aerogels, carbon nanofoams, and lower cost carbon electrodes obtained from pyrolysis of papers. The voltages must be below certain oxidation potential and chemical reaction thresholds. These anions and cations are then sequestered into concentrated brine streams. Voltages used are generally about 0.5 to 1 volt, since at voltages less than that of about 1.23 volts (see Formula 2), no water oxidation occurs and no oxygen is formed at the anode. CDI can be operated at DC power levels as low as 0.5 Volts and 100 mA. However, at these low voltages, the solvated anions and cations migrate to the high surface area electrodes due to the capacitive ion effect, are adsorbed onto their respective electrode surfaces, and held until a polarity reversal releases them, thus separating anions from cations without distillation, reagents, or electrolysis. By adapting this technology to BEC, lower concentrations of carboxylates (VFA salts, VFA-MCFA salts) can be concentrated at high surface area anodes and then electrolytically separated from other anions in aqueous solutions due to the inherently high discharge potentials of carboxylates.

It is also envisioned that an adaptation of a Flow-Through Capacitor (FTC) can be used as a preferred CDI concentration process. Flow-through capacitors use supercapacitors and are specifically designed to separate anions and cations from flowing liquids in an efficient manner at a specific flow rate. An example of a FTC is described in U.S. Pat. No. 6,462,935 (the contents of which are incorporated by reference herein) that possesses conically wound supercapacitor electrode surfaces using ferric oxide and carbon powders.

As a preferred embodiment of the electrolytic stage of the BEC process, it is also envisioned that the CDI concentration and electrolytic processes can be combined together into a CDI/electrolytic process. The CDI process can be adapted to integrate with the electrolytic stage by using lower voltages first to concentrate the carboxylates, and then by using higher voltages, above the critical potential, to perform the electrolysis. This would involve a simple voltage timing-cycle which would allow sufficient time for the carboxylates to concentrate at the anode before performing the actual electrolytic stage. Then the electrolysis would be performed for a time necessary for hydrocarbon conversion until the carboxylate concentration drops (at the anode) to a lower level, which would start the CDI concentration process again. For example, the potential can be held at 1 volt for a sufficient time to concentrate carboxylates (at the anode) at a desired level, and then the voltage can be increased quickly to over 3 volts for a sufficient time to convert carboxylates to hydrocarbons, and then decreased quickly to 1 volt to concentrate carboxylates. These cycles would be repeated until majorities of the carboxylates within a batch are converted to hydrocarbons. In this embodiment, high surface area electrodes are inserted into the fermentation broth with a low applied voltage for a period of time necessary to adsorb and concentrate carboxylate anions at the anode at which point the voltage is increased to commence the electrolysis reaction. This thereby allows the carboxylate concentration process to occur within the VFA fermentation broth and the decarboxylation electrolysis process to be performed in the same vessel. This CDI/electrolysis process may operate at lower current densities (less than 1 mA/cm$^2$) due to the high electrode surface area for a given applied voltage (although higher electrolysis voltages can be used to offset this). However, due to the high carboxylate concentration and the high discharge potentials of carboxylates, decarboxylation electrolysis still occurs even at low current densities. Additionally, the CDI concentration process can include a CDI filter membrane which entirely surrounds the anode within the fermentation broth and separates the anode from the cathode. The CDI filter membrane must be composed of appropriately sized pores which will prevent non-carboxylate anions (larger in size than carboxylate anions of the VFA) from adsorbing onto the anode surface during the CDI concentration process. In this way, many larger sized negatively charged anions within the fermentation broth will be effectively separated from the carboxylate anions during the CDI concentration process. The use of a CDI filter membrane improves carboxylate concentration by removing some non-carboxylate anions that may otherwise inhibit the electrolysis process.

In another embodiment, the CDI method can be used in a separate process to remove VFA (as carboxylate anions) from the fermentation broth during (concurrent with) the primary rumen fermentation (CDI/Fermentation process). In this embodiment, the CDI process is used to decrease the VFA concentration of the fermentation broth and can be used at any time during the primary fermentation process. As VFA concentrations increase within the fermentation broth, the fermentation rate typically decreases. However, use of the CDI/Fermentation process described herein allows the speed of the primary fermentation process to be maximized by removing the VFA during the fermentation. The VFA may be removed continuously or periodically during the fermentation. In a biorefinery process, CDI can be integrated with the fermentation stage in order to continuously or periodically remove VFA from the fermentation broth while separating the fermentation broth from the vessel containing the CDI apparatus. An adaptation of a flow through capacitor (FTC) is preferably used for this purpose. In this embodiment, the electrodes of the CDI or FTC are positioned within the fermentation medium and a low voltage is applied as described above. Again, the carboxylates of the VFA are attracted to and sequestered at the surface of the anode, effectively concentrating the VFA at the locality of the anode and thereby decreasing the VFA concentration in the remainder of the fermentation medium (away from the anode). The VFA adsorbed at the anode may then be converted to hydrocarbons by electrolysis in situ by increasing the voltage in the same manner as described for CDI/electrolysis, or alternatively, the VFA may be recovered for subsequent electrolysis by simply separating the electrodes from the fermentation broth. The electrodes may then be placed in the same or different electrolyte solution-containing vessel and electrolysis conducted to produce hydrocarbons as described above. Alternatively, the VFA may be released from the anode into the electrolyte solution-containing vessel by reversing the polarity of the anode, and the electrolysis performed as described above at a later time. In a particularly preferred configuration, the fermentation medium may be continuously passed across or past the electrodes in a single vessel or multiple vessels connected in series. In this way the rumen microorganisms will be allowed to work at peak efficiency and effectiveness and further decrease total fermentation time.

In yet another embodiment, the CDI/Fermentation process can include a semi-porous membrane that entirely surrounds the CDI anode similar to that used in the CDI concentration process. The purpose of this membrane is to prevent non-carboxylate anions (larger in size than carboxylate anions of the VFA), and other contaminants such as lignins, cells, and proteins from interfering with or adsorbing onto the anode surface during the CDI/Fermentation process.

The electrolysis stage of the process of the invention converts the complete range of the volatile fatty acid products (including any added MCFA) to hydrocarbon and hydrogen fuels. The volatile fatty acids may be converted into large quantities of gas and liquid hydrocarbons and hydrogen gas ($H_2$) using the Kolbe and/or Hofer-Moest reactions of electrochemical decarboxylation. As described above, the Kolbe Reaction is a decarboxylative coupling (dimerization, radical cross coupling), which yields alkanes such as ethane and propane, while the Hofer-Moest Reaction is an oxidative decarboxylation (deprotonation), which yields alkenes such as ethylene and propylene. Both of these reactions occur simultaneously during electrolysis but can be adjusted to favor one reaction or the other by changing several easily controlled variables as described herein below. Different products can be produced by changing these variables, thus allowing a very flexible process.

In accordance with this invention, the electrolysis converts the volatile fatty acids to mixtures of alkanes, alkenes, $H_2$ and $CO_2$ in water, under very mild reaction conditions. For instance, predominant hydrocarbon products of the electrolytic conversion typically include methane and ethane from acetic acid, propane, butane and ethylene from propionic acid, and butane, pentane, hexane and propylene from butyric acid. Mixtures having the same proportions of VFA as the major VFA in the typical in vitro ruminal fermentation noted above (acetate: propionate: butyrate, 6:2:1 molar basis) will yield mixtures of the above products. All reactions will also yield substantial amounts of $H_2$ at the cathode. When other naturally produced organic acids are added to VFA solutions, the number of different hydrocarbon products increases (see Table 1). Hydrocarbon products derived from VFA-MCFA mixtures can include alkanes and alkenes with carbon numbers C5 to C22, including n-octane and kerosene. Likewise, when other organic chemicals such as glycerol, alcohols, and other readily available organic compounds are added to VFA solutions, the number of electrochemical products increases further.

Surprisingly, the electrolysis reactions may be conducted in a simple undivided electrochemical cell under mild electrolysis conditions, at or above 3 volts DC (VDC) and at or above 1 mA/cm$^2$ anode current density, using low-cost carbon or graphite electrodes, at room temperature and ambient pressure, under aqueous conditions. However, when using an integrated CDI/Electrolysis method as described above, the anode current density may be much lower due to the high electrode surface area. For electrolysis conditions, the pH of the aqueous volatile fatty acid solution may range between about 4.5 to 11, preferably between about 5.5 to 8.0. At acidic or neutral pH, Kolbe dimerization to alkanes is favored, while at alkaline pH ranges, Hofer-Moest oxidative deprotonation to alkenes is favored. However, the volatile fatty acids and MCFA need to be in the salt form to be useful for electrolysis. Therefore low pH will tend to decrease volatile fatty acid anion concentration and MCFA solubility. The pH may be adjusted with caustic to maintain a high concentration of acid salts to be electrolyzed. In general, no substrate solvent is needed other than water and no additional organic co-solvents or reagents are required. Moreover, because a major component of the volatile fatty acid produced from biomass is acetic acid, it is itself a useful solvent for anodic electrolytic decarboxylation. Non-aqueous solvents are only required for poorly water soluble reactants (e.g., higher chain MCFA). Methanol, ethanol or isopropanol additions can be used as a substrate solvent for these higher-chain fatty acids (MCFA). Alternatively, due to their relative aqueous insolubilities, these higher-chain fatty acids can be easily separated and processed separately at very high concentrations and therefore can give very high yields of electrolytic products.

The anodic products can be separated from the cathodic products easily during electrolysis by segregating the product receiving vessels from one another. Alternatively, all electrolytic products can be combined easily into a single receiving vessel for further separation or processing. Once collected, the gaseous products (hydrocarbons, $H_2$ and $CO_2$) may be compressed into high pressure tanks and can be further separated into their component products via gas liquefaction. In this manner, carbon dioxide $CO_2$ can be removed easily and sequestered from the hydrocarbon and hydrogen fuel products. In the easiest case possible, all electrolysis products (including $CO_2$) can be combined and used as a fuel in a most field-expedient manner without any further processing.

In contrast to previous studies, the effective conversion of the volatile fatty acids to hydrocarbons by the Kolbe electrolytic reaction conducted in an aqueous medium, using carbon or graphite electrodes at a low current density as described herein, is unexpected. Platinum electrodes and high current densities although desirable, are not required although under certain combinations of reaction conditions they can be used.

In accordance with a preferred embodiment, semi-permeable membranes are provided within the electrolysis cell between (separating) the anode and cathode electrodes. The use of semi-porous membranes allow the current density to increase by decreasing electrode spacing and therefore cell resistance. The membranes permit electrolytes to carry the current while offering good separation of gas products from anode and cathode. Either semi-permeable membranes or salt additions (to provide electrolytes) may be used to decrease cell resistance between the anode and cathode while electronically insulating them from each other, thereby allowing a lower voltage to be used while increasing current density, and improve the product performance. Other semi-porous membranes may be used. The use of a membrane in this manner also allows the electrodes to be positioned near one another, allowing current to flow without arcing. Power for the electrolytic cell may be provided from any convenient source. However, because any voltage above about 3 VDC is adequate for the electrolysis, alternative sources of electricity such as solar cells, wind generators and even fuel cells may be used as power sources to generate hydrocarbons in rural areas or in field-expedient military situations.

For both the Kolbe and the Hofer-Moest decarboxylation reactions, at critical potentials above about 2.0 volts to 2.8 volts for individual carboxylic acids and about 3 volts for carboxylic acid mixtures, and at current densities above 1.0 mA/cm$^2$, no hydroxyl anions are oxidized at the anode and no oxygen gas ($O_2$) is formed (Torii and Tanaka, 2001). This is due to the high discharge potential of carboxylates and because hydroxyl ions are formed at the cathode at the same rate as carboxylate ions are consumed at the anode. Moreover, because the organic acids themselves possess good solvation properties, electrolysis can be carried out in low-cost aqueous solutions without any solvent additions. The products are hydrocarbon mixtures, hydrogen ($H_2$), and carbon dioxide ($CO_2$) gases, along with several other products including alcohols, but without contaminants (e.g., $H_2S$) normally found in natural gas liquids (NGL) exclusively obtained from the petroleum industry.

The selection of the particular electrode material for use in the electrolytic cell is a significant factor in determining which kinds of products will be produced within the electrochemical cell (Torii and Tanaka, 2001, Table 2, p. 505). For instance, electrodes constructed from platinum or porous (amorphous) carbon, favor the Kolbe or Hofer-Moest reactions, respectively. Carbon and graphite electrodes are preferred for use herein, and specific electrode materials that may be used herein include but are not limited to platinum, diamond, vitreous (glassy) carbon, carbon aerogel, carbon nanofoam, graphite, and others. In an industrial application, the preferred electrode material is either platinum or graphite. In order to use graphite electrodes and increase Kolbe products, lower reaction temperatures may be used (Levy et al., 1983). Industrially, platinum coated electrodes are used in PEM cells for the production of hydrogen ($H_2$). These cells may also be used.

Other conditions may also effect the electrolysis reactions and product yields. As noted above, membranes may be used to separate the anode and cathode, and help to decrease or control the electrochemical cell resistance similar to the membranes used in PEM electrolytic cells that produce hydrogen fuels. Additionally, other reaction variables which can be used to enhance product yields and variability within the electrolytic cell include alternating current (waveforms), magnetic fields, and ultrasonic energy, to name a few.

The hydrocarbon products of the electrolysis are spontaneously evolved from solution, and once recovered can be converted to gasoline fractions using well-known and widely practiced industrial chemistry methods (e.g., thermal polymerization), which converts lighter hydrocarbon gases into liquid hydrocarbon fuels. Thermal Polymerization, for example, is a well-known petroleum refining process that converts lighter hydrocarbon gases into liquid hydrocarbon fuels. This involves cracking feedstocks of saturated hydrocarbons (alkanes) to produce unsaturated hydrocarbons (alkenes). Heat and pressure are applied to the alkane feedstocks at the same time, which produces an end product of "Polymer Gasoline" (Speight, 2006). Another refining method that may be used is the Shell Higher Olefin Process (SHOP) of producing desired higher carbon number chain lengths from lower carbon number hydrocarbons. The SHOP process requires ethylene as the feedstock. Ethylene represents a major alkene product that is derived from the VFA salt containing solutions in the invention process. All alkene products are generated by the Hofer-Moest reaction of oxidative electrolytic decarboxylation. Other well-known refining methods such as the Ziegler-Natta reaction and the Wurtz reaction may be also be used to the same effect as well as other known methods. The various products of this invention may be separated either by well-known methods such as fractionally compressing the gaseous products, distilling the liquid products, or filtering the solid products. This is not necessary in all cases, however, because the gaseous products from VFA-salts electrolysis alone will yield NGL (natural gas liquids) when compressed and liquefied. NGL may not need to be separated in order to be valuable, since they can also be used as mixed products.

In addition to the volatile fatty acid products, the fermentation with the ruminal inoculum produces roughly about 10% methane and 20% carbon dioxide as byproducts (based on mass of biomass feedstock) that may be sequestered and reused. The methane may be used to power generators to produce the energy needed in the electrolysis step, or combined with the other hydrocarbon products and refined further. The carbon dioxide produced may be used to deoxygenate the biomass and fermentation medium by displacing air, thereby making it ready for anaerobic fermentation, and may be further sequestered and reused. Alternatively, the $H_2$ and $CO_2$ formed at the cathode and anode electrodes, respectively, can be combined and converted by methanogenic microbes to produce methane gas, or by acetogenic microbes to produce acetic acid. The leftover inorganic salts after electrolysis may be returned to the bioreactor and combined with the next fermentation batch, which may be a continuous process. The solid fermentation residue, including cells and lignin, can be processed into wood-adhesive products (Weimer, U.S. Pat. No. 7,651,582), or used as an animal feed, or used as a fuel to generate electricity for the electrolysis step. The hydrogen ($H_2$) may be used as a fuel or used as a reactant in refining hydrocarbons or other chemicals.

As described herein, nearly all of the conversion products and byproducts produced by the process may be used. There is very little net carbon footprint, because those reactants that come from plant material have already removed the carbon from the atmosphere as opposed to petroleum obtained from beneath the earth. Even the carbon dioxide produced in the conversion process is sequestered, reused and converted to useful products making this invention a truly "Green Process".

Formula 2

Water Electrolysis Reactions

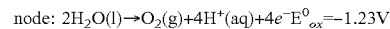

node: $2H_2O(l) \rightarrow O_2(g) + 4H^+(aq) + 4e^- \ E^0_{ox} = -1.23V$

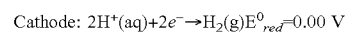

Cathode: $2H^+(aq) + 2e^- \rightarrow H_2(g) \ E^0_{red} = 0.00 \ V$

A significant advantage of the process of this invention is evidenced by a comparison of electrical power needed to produce hydrocarbons from VFA-carboxylic acid solutions (see Formula 1) versus producing hydrogen from water (see. Formula 2). Potential energy as stated here is bond dissociation energy (BDE). As indicated in Table 2, over 8 times more potential energy is obtained using the same amount ($2e^-$) of electrical power, to produce hydrocarbon-hydrogen products from VFA-electrolysis over hydrogen-water electrolysis. For example, ethane and propane produced electrochemically from acetic and propionic acids contain 6 and 9 times, respectively, the potential energy of hydrogen ($H_2$) as a fuel. VFA-MCFA mixtures produce even larger chain hydrocarbon products providing up to 50 times the potential fuel energy of hydrogen-water electrolysis using the same amount of electric power. For example, a MCFA like C16 palmitic acid, mixed with VFAs in an electrolytic cell will produce up to C18 hydrocarbons (n-octadecane) in carbon chain length through Kolbe cross-radical coupling, which yields a BDE 50-times that of hydrogen using the same amount of electrical power.

The following examples are intended only to further illustrate the invention and are not intended to limit the scope of the invention that is defined by the claims.

Example 1

A mixed microbial consortium obtained from bovine ruminal fluid was fermented in vitro with eastern gamagrass (a harvested native grass) or alfalfa (harvested legume crop). Both are representative of a perennial cellulosic biomass feedstock. Separation of the resulting fermentation broth containing VFAs, from the solid residue (including cells and lignin) was accomplished by filtration and/or centrifugation.

The electrolytic apparatus was generally comprised of a simple undivided cell with carbon or graphite plates or rods used for both anode and cathode electrodes. Platinum anodes were also used for comparison purposes. Stainless steel and other metal electrode material were also used for cathodes. Although many anode materials can be used, carbon/graphite electrodes were selected in addition to platinum anodes, for example, due to their low cost and effectiveness on an industrial scale. The electrodes were immersed directly into the fermentation broth which generally had a pH range of about 5.5-6.5 at room temperature. pH adjustment was performed in some cases to bring the pH range to about 6.0-6.5 to increase the carboxylic salt concentration. Electrical potentials were kept above 3 volts DC so that oxygen production at the anode was eliminated. It is known that aqueous solutions of salts of carboxylic acids, that is, carboxylate anions, form a film on the anode electrode surface at a specific critical voltage potential that prevents any oxidation of the hydroxyl ion from the aqueous solution. The critical potentials (from the Tafel equation and Tafel plots) for decarboxylation of a variety of carboxylic acids are within a range of about 2.0 volts to 2.8 volts (Torii and Tanaka, 2001, FIG. 1, p. 502). In practice, the electrolysis can be performed at any voltages that exceed these critical potentials for the respective individual carboxylic acids. As a general rule for various aqueous carboxylic acid mixtures, it is practical to keep electrical potentials above about 3 volts DC which exceeds the 2.8 volts higher threshold critical potential for carboxylates.

Fine mesh porous nylon membranes (to minimize electrode spacing) and salts additions (to provide electrolytes) were used to decrease cell, resistance, which allows a lower voltage to be used while increasing current density, and improved the product performance. Other semi-porous membranes may be used. Membranes permit electrolytes to carry the current while offering good separation of gas products from anode and cathode. Gases were collected above the anode by liquid displacement of the fermented broth samples from Balch tubes (Balch and Wolfe, 1986), which were positioned over the respective anode and cathode. The tubes were then sealed with butyl rubber stoppers while still immersed in the liquid of the electrolysis cell, after which the stoppers were sealed with aluminum crimp seals.

Electrolytic cell resistance can be higher without the use of porous or semi-porous membranes or electrolytes because electrodes need to be separated at greater distances to prevent anode/cathode gas products from mixing. Anode current density can be increased to higher levels by decreasing electrode spacing with porous or semi-porous membranes, or by adding MCFA salts or NaCl to the substrate. The electrolytic cell can be adjusted to deliver any current level desired by varying the applied potential, electrode surface area, electrode spacing, substrate concentration, electrolytes and other factors. Current densities at the electrode surfaces are a key factor in electrochemical cell performance. The current density may be balanced equally between anode and cathode or may be designed to be unbalanced. For example, decreasing the anode surface area or increasing the cathode surface area for the same cell current may increase anode current density. Products and yields can differ and can be controlled using different anode current densities. For example, at lower current densities and higher voltage potentials, alkenes (Hofer-Moest products) are favored over alkanes. At higher anode current densities and lower voltage potentials, alkanes (Kolbe products) are favored over alkenes. There is an inherent flexibility in this invention to tailor products by varying fermentation and electrolytic conditions.

For experimental purposes, voltages of above 3 VDC with 1 mA/cm$^2$-100 mA/cm$^2$ anode current density were used depending on the cell resistance due to electrode spacing within the fermented broth. The literature (Torii and Tanaka, 2001) suggests that higher anode current densities of about 250 mA/cm$^2$ and higher, produce more Kolbe products. However, it was the intention of this research to run electrolyses on the primary fermentation broths with very simple equipment in order to prove process efficacy with minimum possible costs.

Hydrocarbon products derived from VFA mixtures alone include: ethane, propane, butane, pentane, hexane, ethylene, and propylene. In addition, pure hydrogen gas ($H_2$) is produced in large quantities, as well as carbon dioxide, which can be sequestered and reused in the deoxygenation/air displacement step. Hydrocarbon products derived from VFA-MCFA mixtures can include alkanes and alkenes with carbon numbers C5 to C20, including n-octane and kerosene (see Table 1).

I. Biological Stage (Fermentation)

Example Bio-1

Fermentation of Eastern Gamagrass to VFA

A flask containing 600 mL of Goering-Van Soest medium (Goering and Van Soest, 1970; contents per liter: 8.75 g $NaHCO_3$, 1.0 g $NH_4HCO_3$, 1.55 g $KH_2PO_4$, 1.43 g $Na_2HPO_4$, 0.15 g $MgSO_4$), 16.4 g of air-dried Eastern gamagrass (ground in a Wiley mill having a 1 mm screen), 1.0 g of Trypticase, and 0.002 g of resazurin, was gassed under a stream of $CO_2$, after which 0.6 g of cysteine HCl and 0.05 g of $Na_2S.9H_2O$ was added. The flask was inoculated with rumen contents (~80 mL of liquid and 20 g squeezed solids) prepared by mixing similar amounts from two rumen-fistulated cows. The flask was incubated at 39° C. without shaking. After 54 h incubation, samples were removed for fermentation product analysis. Samples were centrifuged at 10,000×g for 10 min, and 600 uL of the supernatant liquid was combined with 600 uL of CHS (26.45 g $Ca(OH)_2$ added to 100 mL $H_2O$) and 300 uL of CSR (10 g $CuSO_4$+0.4 g crotonic acid per 100 mL aqueous solution). The mixture was frozen, thawed and centrifuged. The supernatant liquid was transferred to tubes containing 28 uL of $H_2SO_4$, and this solution, frozen and thawed twice, then centrifuged. The supernatant liquid was analyzed by high performance liquid chromatography (HPLC), using a 250 mm×4.6 mm Bio-Rad Aminex HPX-87H analytical column maintained at 45° C. Samples (50 uL) were eluted with a mobile phase of 0.015 $NH_2SO_4$/0.0034 M ethylenediaminetetracetic acid (EDTA) at a flow rate of 0.7 mL/min, and separated peaks were detected with a refractive index detector. Quantification was achieved by comparison to standard curves, with crotonic acid as internal standard. After incubation the culture contained 77.5 mM acetic, 21.7 mM propionic, 8.8 mM butyric, 1.4 mM isobutyric, 2.7 mM valeric, and 2.4 mM of a combination of 2-methylbutyric and 3-methylbutyric acids.

Example Bio-2

Production of VFA in Stable Enrichment Cultures

The culture from Example Bio-1 was sequentially transferred for 7 successive transfers of ~50 g of liquids and solids at 2 to 3 d. The culture medium was the same as described in Example Bio-1, except incubations were conducted at one-half volumetric scale (300 mL medium), and the Trypticase was replaced by dried distillers grains (DDG). After 28 h incubation at 39° C. without shaking, fermentation broth samples were collected and analyzed as described in Example Bio-1. The amounts of fermentation products in the cultures were 113.9 mM acetic, 33.6 mM propionic, 10.3 mM butyric, 0.6 mM isobutyric, 2.0 mM valeric, and 1.0 mM of a combination of 2-methylbutyric and 3-methylbutyric (isovaleric) acids.

Example Bio-3

VFA Production from Biomass Feedstocks by Stabilized Mixed Cultures of Ruminal Microorganisms Fermentations were conducted at 39° C. in unshaken Erlenmeyer flasks in 150 mL of a Goering/Van Soest medium supplemented with 4 g dried biomass feedstock (Eastern gamagrass or alfalfa, ground through a 1 mm Wiley mill screen but otherwise not pretreated) and 0.5 g of DDG. Flasks were gassed with $CO_2$ prior to inoculation but were incubated with vented closures, without additional gas sparging, during the fermentation. Cultures were transferred at intervals of 2 to 4 days by pouring ~20% by volume of culture from the previous culture to a flask containing fresh medium. VFA concentrations were determined in culture supernatants obtained by centrifugation of 2- to 4-d old cultures at 12,000×g for 10 min. Results are shown in Table B-1.

TABLE B-1

VFA concentrations in stabilized enrichment cultures or mixed ruminal microflora grown on Eastern gamagrass (EGG) or alfalfa (Alf). The number code for the Eastern gamagrass (EGG) and alfalfa (Alf) cultures corresponds to the sequential transfer number of the culture after the original ruminal inoculation.

| Additions | Acetic | Propionic | Butyric | $IB^a$ | IV + $2MB^b$ | Valeric | Total |
|---|---|---|---|---|---|---|---|
| EGG-32 | 102.6 | 32.8 | 14.8 | 0.5 | 0.5 | 2.0 | 153.2 |
| EGG-57 | 111.8 | 32.4 | 13.7 | 0.4 | 0.7 | 4.8 | 163.8 |
| EGG-97 | 110.8 | 38.7 | 12.2 | 0.6 | 0.7 | 3.6 | 166.7 |
| EGG-141 | 93.9 | 25.0 | 10.6 | 1.4 | 5.0 | 2.5 | 138.3 |
| Alf-11 | 71.1 | 31.2 | 7.6 | 1.8 | 4.0 | 3.3 | 118.8 |
| Alf-23 | 73.5 | 23.9 | 9.2 | 1.0 | 3.3 | 2.1 | 113.0 |

$^a$IB = isobutyric
$^b$IV + 2MB = isovaleric (3-methylbutyric) acid plus 2-methylbutyric Example Bio-4

In Vitro VFA Production from Fermentation of Biopolymers by Mixed Ruminal Microorganisms Collected from Ruminally-Fistulated Cows Fermentations were conducted under a $CO_2$ gas phase in sealed vials containing 100 mg of substrate in 8.5 mL of a Goering/Van Soest medium (except for DNA, 7.2 mg in 1.9 mL medium) supplemented with 1 g of Trypticase per liter plus 1.5 mL of freshly-collected ruminal inoculum (0.3 mL for DNA) squeezed through cheesecloth to remove large feed particles. Results are shown in Tables B-2 and B-3.

TABLE B-2

Net VFA production from ~0.10 g of various biopolymers by mixed ruminal microorganisms sampled directly from ruminally fistulated cows. Values corrected for VFA production in blank vials containing ruminal inoculum but lacking added substrate. Fermentations of the same substrates with adapted ruminal enrichment cultures gave substantially similar results.

| Substrate | Acetic | Propionic | Butyric | $IB^b$ | IV + $2MB^c$ | Valeric | Total |
|---|---|---|---|---|---|---|---|
| Cellulose | 41.0 | 43.5 | 4.3 | 0.6 | 0.5 | 1.4 | 91.3 |
| Tobacco stalk xylan | 43.1 | 33.5 | 3.1 | 0 | 0 | 0.8 | 80.5 |
| Birch xylan | 50.9 | 34.8 | 3.8 | 0.1 | 0 | 0.7 | 90.2 |
| CS hemicellulose | 39.1 | 31.5 | 3.1 | 0 | 0 | 0.8 | 74.5 |
| Corn starch | 37.4 | 32.9 | 6.8 | 0 | 0.2 | 2.0 | 79.2 |
| Fructan | 16.7 | 13.2 | 3.5 | 0 | 0 | 0.8 | 34.1 |
| Alfalfa pectin | 17.5 | 5.9 | 1.2 | 0.2 | 0.3 | 0.5 | 25.5 |
| Microbial cells | 16.9 | 3.5 | 1.9 | 0.9 | 2.7 | 1.3 | 27.7 |
| Soybean peptone | 22.6 | 7.8 | 8.4 | 3.5 | 8.7 | 7.1 | 58.0 |
| Distillers grains | 26.7 | 19.4 | 4.5 | 0.6 | 1.5 | 2.5 | 55.2 |
| DNA (7.2 mg) | 0.78 | 0.4 | 0.93 | 0.08 | 0 | 0 | 1.9 |

$^a$Substrates: CS hellulose purified from stalks of cicer milkvetch (*Astragalus cicer*). Fructan from orchardgrass (*Dactylis glomerata*); Microbial cells from ruminal contents.
$^b$IB = isobutyric
$^c$IV + 2MB = isovaleric (3-methylbutyric) acid plus 2-methylbutyric

TABLE B-3

Fractional yield (g VFA per g dry weight of added substrate) from fermentation of various biopolymers by mixed ruminal microorganisms sampled from ruminally fistulated cows. Total VFA yield on a weight basis varied from 14.5 to 66.1%, depending on substrate.

| | g VFA per g dry weight of added substrate | | | | | | |
|---|---|---|---|---|---|---|---|
| Substrate | Acetic | Propionic | Butyric | IB[b] | IV + 2MB[c] | Valeric | Total |
| Cellulose | 0.258 | 0.337 | 0.040 | 0.006 | 0.005 | 0.015 | 0.661 |
| Tobacco stalk xylan | 0.297 | 0.285 | 0.031 | 0 | 0 | 0.003 | 0.615 |
| Birch xylan | 0.334 | 0.282 | 0.036 | 0.001 | 0 | 0.008 | 0.656 |
| CS hemicellulose | 0.253 | 0.251 | 0.029 | 0 | 0 | 0.008 | 0.534 |
| Corn starch | 0.250 | 0.271 | 0.066 | 0 | 0.002 | 0.023 | 0.612 |
| Fructan | 0.115 | 0.112 | 0.035 | 0 | 0 | 0.009 | 0.266 |
| Alfalfa pectin | 0.337 | 0.140 | 0.034 | 0.006 | 0.010 | 0.015 | 0.542 |
| Microbial cells | 0.104 | 0.027 | 0.017 | 0.008 | 0.028 | 0.014 | 0.198 |
| Soybean peptone | 0.154 | 0.065 | 0.084 | 0.035 | 0.101 | 0.082 | 0.520 |
| Distillers grains | 0.182 | 0.162 | 0.044 | 0.006 | 0.018 | 0.029 | 0.441 |
| DNA | 0.052 | 0.033 | 0.090 | 0.008 | 0 | 0 | 0.145 |

[a]Substrates: CS = hemicellulose purified from stalks of cicer milkvetch (*Astragalus cicer*). Fructan from orchardgrass (*Dactylis glomerata*); Microbial cells from ruminal contents.
[b]IB = isobutyric
[c]IV + 2MB = isovaleric (3-methylbutyric) acid plus 2-methylbutyric Example Bio-5

Fermentation of Other Polysaccharides

Polysaccharides (100 mg fresh weight) were fermented for 24 h at 39° C. under a $CO_2$ atmosphere in sealed, unshaken vials that contained 8.5 mL of Goering/Van Soest buffer and 1.5 mL of squeezed ruminal fluid. Subsamples of culture were centrifuged and the supernatant assayed for VFA by HPLC. Results are shown in Table B-4. Total VFA yield on a weight basis varied from 50.9 to 78.7%, depending on substrate.

TABLE B-4

Fermentation of carbohydrates by mixed ruminal microflora. Results are corrected for VFA produced in vials containing ruminal inocula but lacking added carbohydrate.

| | g of VFA per g dry weight of added polysaccharide | | | | | | |
|---|---|---|---|---|---|---|---|
| Carbohydrate | Acetic | Propionic | Butyric | IB[a] | IV + 2MB[b] | Valeric | Total |
| Cellulose | 0.317 | 0.347 | 0.034 | 0.007 | 0.003 | 0.013 | 0.722 |
| Chitin | 0.417 | 0.063 | 0.015 | 0.009 | 0.001 | 0.004 | 0.509 |
| Fructan | 0.265 | 0.326 | 0.146 | 0.001 | 0 | 0.062 | 0.787 |
| Fructose | 0.227 | 0.245 | 0.119 | 0.002 | 0 | 0.047 | 0.631 |
| Sucrose | 0.236 | 0.285 | 0.124 | 0 | 0 | 0.059 | 0.691 |
| Glucosamine | 0.210 | 0.303 | 0.088 | 0.004 | 0 | 0.018 | 0.620 |

[a]IB = isobutyric
[b]IV + 2MB = isovaleric (3-methylbutyric) acid plus 2-methylbutyric Example Bio-6

Augmentation of Mixed Ruminal Microflora Cultures with Ethanol or Additional Bacteria to Shift VFA Product Ratios Sealed vials containing 8.5 mL or Modified Dehority medium and microcrystalline cellulose (95 mg dry weight) under a $CO_2$ atmosphere were amended with additional substrate or an enrichment culture of *Clostridium kluyveri*-like bacteria (Ckb). Vials were incubated at 39° C. without shaking for 72 h, after which subsamples of the gas phase were withdrawn for analysis by gas chromatography, and subsamples of liquid phase were withdrawn and centrifuged, and the supernatant phase analyzed for VFA by HPLC. Results are shown in Table B-5 and B-6.

TABLE B-5

VFA production from cellulose fermentations amended with ethanol and/or enrichment cultures of *Clostridium kluyveri*-like bacteria. Results are corrected for VFA produced in vials containing ruminal inocula but lacking added cellulose, ethanol or Ckb[a].

| | net mM VFA produced | | | | | | |
|---|---|---|---|---|---|---|---|
| Additions | Acetic | Propionic | Butyric | IB[b] | IV + 2MB[c] | Valeric | Caproic |
| None | 41.3 | 41.1 | 3.0 | 0.7 | 0.4 | 1.2 | 0 |
| Ethanol (0.1 ml) | 38.6 | 34.8 | 3.1 | 0.7 | 0 | 1.9 | 0 |
| Ckb[a] | 38.7 | 40. | 2.0 | 0.4 | 0.5 | 1.9 | 0.5 |
| Ethanol + Ckb[a] | 39.5 | 31.9 | 1.1 | 0.4 | 0 | 4.7 | 1.3 |

[a]Ckb = Enrichment culture containing *Clostridium kluyveri*-like bacteria. Enrichment culture was prepared by inoculation of ruminal contents from lactating dairy cows into a modified Dehority medium (Weimer et al., 1991) supplemented with ethanol, acetic acid and succinic acid; these culture was transferred at 2- to 4-week intervals of incubation at 39° C.
[b]Isobutyric
[c]IV + 2MB = isovaleric (3-methylbutyric) acid plus 2-methylbutyric

TABLE B-6

Gas production in cellulose fermentations amended with ethanol and/or cultures of *Clostridium kluyveri*-like bacteria. Results are corrected for gas produced in vials containing ruminal inocula but lacking added cellulose, ethanol or Ckb [a]

| | mmoles gas per mol anhydroglucose added | |
|---|---|---|
| Addition | $H_2$ | $CH_4$ |
| None | 0.85 | 232 |
| Ethanol (0.1 mL) | 1.19 | 264 |
| Ckb [a] | 0.49 | 525 |
| Ethanol + Ckb [a] | 0.88 | 333 |

[a] Ckb = Enrichment culture containing *Clostridium kluyveri*-like bacteria.

Example Bio-7

Shift to Longer Chain VFAs Resulting of Co-Fermentation with Glycerol

Sealed vials containing 8.5 mL of Goering and Van Soest medium plus microcrystalline cellulose (95 mg dry weight) under a $CO_2$ atmosphere were amended with additions as indicated. Vials were incubated at 39° C. without shaking for 24 h, after which subsamples of liquid phase were withdrawn for analysis of VFA by HPLC. Results are shown in Table B-7.

TABLE B-7

VFA production from cellulose fermentations amended with glycerol and/ or ethanol. Results are corrected for VFA produced in vials containing ruminal inoculum but lacking added cellulose, glycerol or ethanol.

| | net mM VFA produced | | | | | | |
|---|---|---|---|---|---|---|---|
| Additions | Acetic | Propionic | Butyric | IB[a] | IV + 2MB[b] | Valeric | Total |
| None | 34.7 | 36.5 | 2.8 | 0.2 | 0.4 | 1.0 | 75.5 |
| Glycerol (0.1 mL) | 27.7 | 64.2 | 7.4 | 0 | 0 | 2.6 | 101.9 |
| Ethanol (0.1 mL) | 43.8 | 34.0 | 1.4 | 0 | 0 | 0.7 | 165.6 |
| Glycerol + Ethanol | 31.5 | 52.8 | 9.7 | 0 | 0 | 2.0 | 162.4 |

[a]IB = isobutyric
[b]IV + 2MB = isovaleric (3-methylbutyric) acid plus 2-methylbutyric

II. Electrolytic Stage (Electrochemical)

The electrolytic conditions used for examples Elec-1 and Elec-2 below, were a high-temperature graphite electrode plate (2 cm×3 cm) for the anode, and a stainless steel plate (2 cm×3 cm) for the cathode. Electrode spacing was 1 mm using a nylon mesh membrane. Substrate volume was 250 mL, with no pH adjustment. In these examples, $CO_2$ was produced at the anode along with the hydrocarbon products noted, and $H_2$ was produced at the cathode.

Example Elec-1

Electrolysis of Centrifuged (Unfiltered) Fermentation Broth

Centrifuged (11,300×g, 30 min) samples from the broth of an in vitro fermentation of eastern gamagrass were pooled from several separate fermentations using adapted ruminal inocula, to provide enough volume to nearly fill the electrolysis cell. These supernatants were subjected to the following electrolysis conditions:

| | |
|---|---|
| Current Density | 60 mA/cm² |
| pH | 5.5-5.7 |
| Temperature | 25° C. |

Samples of the gas phase were withdrawn using a hypodermic syringe and analyzed by gas chromatography. In the gas chromatograph helium carrier gas (18 mL/min) was used to separate the analytes through a Restek Q-BOND capillary column (30 m×0.25 mm) prior to detection by a flame ionization detector operated at 240° C. The chromatographic conditions included an injector split ratio of 30:1, a temperature program of the column oven (50° C. to 240° C. at 8° C./min, with a final hold at 240° C. for 10 min). Chromatographic peaks were compared to those of known standards. Identified gaseous anodic products included n-alkanes (methane, ethane, propane, pentane, hexane), branched alkanes (2-methylpentane, 3-methylpentane) and alkenes (ethylene, propylene, cis-2-pentene).

Example Elec-2

Electrolysis of Filtered Fermentation Broth

Fermentation broth obtained by in vitro fermentation of eastern gamagrass was subjected to filtration through nylon mesh screen, followed by hollow fiber filtration through a 0.2 um pore size cartridge. The permeate was further subjected to ultrafiltration through a nominal 10,000 Da-molecular weight cutoff (10 kDa NMWCO) cartridge to produce a liquid permeate containing VFAs, and a concentrated protein retentate fraction. The liquid permeate (VFA concentration=135 mM) was subjected to the following electrolysis conditions:

| | |
|---|---|
| Current Density | 70-80 mA/cm² |
| pH | 5.9-6.1 |
| Temperature | 20° C. |

Gases were collected and analyzed as described in Example Elec-1. Identified gaseous anodic products included n-alkanes (methane, ethane, propane, hexane), branched alkanes (2-methylpentane) and alkenes (ethylene, propylene, cis-2-pentene).

The electrolytic conditions used for example Elec-3 below, were a coiled, fine platinum electrode wire (0.033 cm dia.×120 cm long) for the anode, and a stainless steel plate (2.5 cm×5 cm) for the cathode. Electrode spacing was 3 mm using a nylon mesh membrane. Substrate (butanol extract) volume was 250 mL, with KOH pH adjustment and a cooler starting/ending temperature. In this example, $CO_2$ was produced at the anode along with the hydrocarbon products noted, and $H_2$ was produced at the cathode.

Example Elec-3

Electrolysis of a Butanol Extract of Filtered Fermentation Broth

Ultrafiltered fermentation broth (3.00 liters) from Example Elec-1 above was adjusted to pH 3.25 with concentrated HCl, flushed with $N_2$ gas, then extracted with 788 g of n-butanol. The butanol phase (713 g) was recovered and amended with 200 mL of $H_2O$. After adjusting pH to 8.2 with 10 N NaOH, 200 mL of additional $H_2O$ was added. The butanol and water phases were allowed to separate, and the aqueous phase (containing most of the VFAs) was recovered.

The butanol extract was subjected to the following electrolysis conditions:

| | |
|---|---|
| Current Density | 50 mA/cm² |
| pH | 6.7 |
| Temperature | 10-17° C. |

Gases were collected and analyzed as described in Example Elec-1. Identified gaseous anodic products included n-alkanes (methane, ethane, propane, butane, pentane, hexane), branched alkanes (2-methylpentane, 3-methylpentane) and alkenes (ethylene, propylene, cis-2-pentene).

It is understood that the foregoing detailed description is given merely by way of illustration and that modifications and variations may be made therein without departing from the spirit and scope of the invention.

TABLE 1

Hydrocarbon Products from Electrochemical
Oxidative Decarboxylation of VFA and MCFA Mixtures

| Carboxylic (Fatty) Acids | Carbon-Chain Length | Electrochemical Kolbe[1] Products (Alkanes) | Carbon-Chain Length | Physical Properties @ Room Temp. | Electrochemical Hofer-Moest[2] Products (Alkenes) | Carbon-Chain Length | Physical Properties @ Room Temp. |
|---|---|---|---|---|---|---|---|
| VFA* Mixtures | | | | | | | |
| Acetic | C2 | Methane | C1 | Gas | — | — | — |
|  |  | Ethane | C2 | Gas | — | — | — |
| Propionic | C3 | Propane | C3 | Gas | Ethylene | C2 | Gas |
|  |  | n-Butane | C4 | Gas |  |  |  |
| Butyric | C4 | n-Butane | C4 | Gas | Propylene | C3 | Gas |
|  |  | n-Pentane | C5 | Liquid | — | — | — |
|  |  | n-Hexane | C6 | Liquid | — | — | — |
| VFA-MCFA** Mixtures | | | | | | | |
| Valeric[3] | C5 | n-Pentane | C5 | Liquid | 1-Butene | C4 | Liquid |
|  |  | n-Hexane | C6 | Liquid | — | — | — |
|  |  | n-Heptane | C7 | Liquid | — | — | — |
| Caproic | C6 | n-Hexane | C6 | Liquid | 1-Pentene | C5 | Liquid |
|  |  | n-Heptane | C7 | Liquid | — | — | — |
|  |  | n-Octane | C8 | Liquid | — | — | — |
| Caprylic | C8 | n-Octane | C8 | Liquid | 1-Heptene | C7 | Liquid |
|  |  | n-Nonane | C9 | Liquid | — | — | — |
|  |  | n-Decane | C10 | Liquid | — | — | — |
| Capric | C10 | n-Decane | C10 | Liquid | 1-Nonene | C9 | Liquid |
|  |  | n-Undecane | C11 | Liquid | — | — | — |
|  |  | n-Dodecane | C12 | Liquid | — | — | — |
| Lauric | C12 | n-Dodecane | C12 | Liquid | Higher α-Alkenes | C11 | Liquid |
|  |  | n-Tridecane | C13 | Liquid | — | — | — |
|  |  | n-Tetradecane | C14 | Liquid | — | — | — |
| Myristic | C14 | n-Tetradecane | C14 | Liquid | Higher α-Alkenes | C13 | Liquid |
|  |  | n-Pentadecane | C15 | Liquid | — | — | — |
|  |  | n-Hexadecane | C16 | Liquid | — | — | — |
| Palmitic | C16 | n-Hexadecane | C16 | Liquid | Higher α-Alkenes | C15 | Liquid |
|  |  | n-Heptadecane | C17 | Solid | — | — | — |
|  |  | n-Octadecane | C18 | Solid | — | — | — |
| Stearic, Oleic, Linoleic | C18:0 C18:1 C18:2 | Higher Alkanes | C18 C19 C20 | Solid | Higher Alkenes, Dienes, and Trienes | C17 | Solid |

*Volatile Fatty Acids - From Ruminal Fermentation Contain Acetic, Propionic, and Butyric Carboxylic Acids
**Medium Chain Fatty Acids - Additions of MCFA to VFA Yield Higher Carbon-Chain Hydrocarbons
[1]Kolbe Reaction is One-Electron Oxidation of Carboxylic Acids Yielding Alkanes (Dimers, Cross-Radicals)
[2]Hofer-Moest Reaction is Two-Electron Oxidation of Carboxylic Acids Yielding Alkenes (Deprotonation)
[3]Valeric, Iso-Valeric, 2-Methyl Butyric, and Iso-Butyric Acids are also produced in Ruminal Fermentation and represent 3% to 5% of total VFA.
Note: Higher carbon-chain fatty acids may require solvent additions, such as methanol, instead of carrying out electrolysis in aqueous solutions due to there relative insolubility in water.

TABLE 2

Potential Energy-Bond Dissociation Energy (BDE) Fuel Product Comparison-
Electrolysis of Water to Hydrogen vs. VFA-Carboxylic Acids to Hydrocarbons
(Using the Same Amount of Electrical Energy):

BDE/mol-Hydrogen Electrolysis from Water:

Cathode: $2H^+(aq) + 2e^- \rightarrow H_2$ (gas)　　　　　　　　　　　436 kJ/mol BDE

BDE/mol-Kolbe Electrolysis Products from VFA Mixture:
(Assuming R-R = 6:2:1 VFA molar Ratio of Acetic, Propionic, Butyric Acids)

| | |
|---|---|
| Anode: $2RCO_2^-(aq) \rightarrow R\text{-}R$ (gas) $+ 2e^-$ | 3346 kJ/mol BDE |
| Cathode: $2H^+(aq) + 2e^- \rightarrow H_2$ (gas) | 436 kJ/mol BDE |
| Total BDE | 3782 kJ/mol BDE = (8.7 Times $H_2$) |

TABLE 2-continued

Energy Value (kJ/mol)-Electrolysis from Volatile Fatty Acids (VFA) Alone:

| VFA to Fuel | Molar Ratio | Total BDE | Total BDE/mol |
|---|---|---|---|
| Ethane | 6 | 2825 | 1883 |
| Propane | 2 | 3998 | 888 |
| Butane | 1 | 5171 | 575 |
| | | Total Hydrocarbons | 3346 |
| Hydrogen | 1 | 436 | 436 |
| | | Total Fuel | 3782 (8.7 Times $H_2$) |

Energy Value (kJ/mol)-Electrolysis from Mixtures of Volatile Fatty Acids (VFA) And Medium Chain Fatty Acids (MCFA) Compared to Hydrogen:

| VFA/MCFA to Fuel | Carbon Chain | Total BDE | BDE Ratio to Hydrogen |
|---|---|---|---|
| Ethane | C2 | 2825 | 6:1 |
| Propane | C3 | 3998 | 9:1 |
| Butane | C4 | 5171 | 12:1 |
| Pentane | C5 | 6344 | 15:1 |
| Hexane | C6 | 7517 | 17:1 |
| Heptane | C7 | 8690 | 20:1 |
| Octane | C8 | 9863 | 23:1 |
| Nonane | C9 | 11036 | 25:1 |
| Decane | C10 | 12209 | 28:1 |
| Dodecane | C12 | 14555 | 33:1 |
| Tetradecane | C14 | 16901 | 39:1 |
| Hexaadecane | C16 | 19247 | 44:1 |
| Octadecane | C18 | 21593 | 50:1 |
| Hydrogen | 0 | 436 | 1:1 |

TABLE 3

Fatty acid composition of some plant oils and animal fats of commercial importance.[1]

| Oil or Fat | Capric Acid C10:0 | Lauric Acid C12:0 | Myristic Acid C14:0 | Palmitic Acid C16:0 | Stearic Acid C18:0 | Oleic Acid C18:1 | Linoleic Acid (ω6) C18:2 | Alpha Linolenic Acid (ω3) C18:3 |
|---|---|---|---|---|---|---|---|---|
| Beef Tallow | — | — | 3 | 24 | 19 | 43 | 3 | 1 |
| Canola Oil | — | — | — | 4 | 2 | 62 | 22 | 10 |
| Cocoa Butter | — | — | — | 25 | 38 | 32 | 3 | — |
| Cod Liver Oil | — | — | 8 | 17 | — | 22 | 5 | — |
| Coconut Oil | 6 | 47 | 18 | 9 | 3 | 6 | 2 | — |
| Corn Oil (Maize Oil) | — | — | — | 11 | 2 | 28 | 58 | 1 |
| Cottonseed Oil | — | — | 1 | 22 | 3 | 19 | 54 | 1 |
| Flaxseed Oil | — | — | — | 3 | 7 | 21 | 16 | 53 |
| Lard (Pork fat) | — | — | 2 | 26 | 14 | 44 | 10 | — |
| Olive Oil | — | — | — | 13 | 3 | 71 | 10 | 1 |
| Palm Oil | — | — | 1 | 45 | 4 | 40 | 10 | — |
| Palm Kernel Oil | 4 | 48 | 16 | 8 | 3 | 15 | 2 | — |
| Peanut Oil | — | — | — | 11 | 2 | 48 | 32 | — |
| Safflower Oil | — | — | — | 7 | 2 | 13 | 78 | — |
| Sesame Oil | — | — | — | 9 | 4 | 41 | 45 | — |
| Soybean Oil | — | — | — | 11 | 4 | 24 | 54 | 7 |
| Sunflower Oil | — | — | — | 7 | 5 | 19 | 68 | 1 |

[1]Adapted from Zamora (2005). Composition varies slightly with varietal source and growth conditions.

TABLE 4

Fatty acid composition of some *Cuphea* seed oils and of coconut oil.[1]

| Species | C8 (Caprylic) | C10 (Capric) | C12 (Lauric) | C14 (Myristic) | Others |
|---|---|---|---|---|---|
| C. carthagenensis | | 5.3 | 81.4 | 4.7 | 8.6 |
| C. epilobiifolia | 0.3 | 19.6 | 67.9 | | 12.2 |
| C. hookeriana | 65.1 | 23.7 | 0.1 | 0.2 | 10.9 |
| C. laminuligera | | 17.1 | 62.6 | 9.5 | 10.8 |

TABLE 4-continued

Fatty acid composition of some *Cuphea* seed oils and of coconut oil.[1]

| Species | Distribution (% of total fatty acids) | | | | |
|---|---|---|---|---|---|
| | C8 (Caprylic) | C10 (Capric) | C12 (Lauric) | C14 (Myristic) | Others |
| *C. lanceolata* | | 87.5 | 2.1 | 1.4 | 9 |
| *C. lutea* | 0.4 | 29.4 | 37.7 | 11.1 | 21.4 |
| *C.. koehneana* | 0.2 | 95.3 | 1 | 0.3 | 3.2 |
| *C. painteri* | 73 | 20.4 | 0.2 | 0.3 | 6.1 |
| *C. stigulosa* | 0.9 | 18.3 | 13.8 | 45.2 | 21.8 |
| *C. viscosissima* | 9.1 | 75.5 | 3 | 1.3 | 11.1 |
| *C. wrightii* | | 29.4 | 53.9 | 5.1 | 11.6 |
| Coconut oil | 8 | 7 | 48 | 18 | 19 |

[1] Adapted from Kleiman, 1990.

TABLE 5

Chemical analysis of oil from *Jatropha curcas* L.[1]

| | Type I | Type II | Type III |
|---|---|---|---|
| Free fatty acid content | 0.03% | 0.18% | 3.69% |
| Color (5¼" Lovibond) | 17 yellow; 1, red | 14 yellow; 1, 4 red | |
| Viscosity @ 100° F. | 38.8 CST | 37 CST | |
| Saponification number | 195.5 | 193.6 | 192 |
| Iodine number | 94.9 | 105.2 | 96 |
| Fatty Acid Profile in % | | | |
| Palmitic (C16:0) | 14.6 | 3.45 | 15.6 |
| Stearic (C18:0) | 7.15 | 7.46 | 6.7 |
| Oleic (C18:1) | 46.27 | 34.3 | 42.6 |
| Linoleic (C18:2) | 30.8 | 43.12 | 33.9 |
| Others | 0.2 | 0.2 | 0.2 |

[1] Adapted from Lele, 2006.

BIBLIOGRAPHY

Balch, W. E., and R. S. Wolfe. 1976. New approach to the cultivation of methanogenic bacteria: 2-mercaptoethanesulfonic acid (HS-CoM)-dependent growth of *Methanobacterium ruminantium* in a pressurized atmosphere. Appl. Environ. Microbiol. 32:781-791.

Bradin, D. 2007. Production of gasoline from fermentable feedstocks. International Patent Publication Number WO 2007/095215 A2. International Patent Application Published Under the Patent Cooperation Treaty (PCT) of the World Intellectual Property Organization.

Goering, H. K., and P. J. Van Sorest. 1970. Forage Fiber Analysis (Apparatus, Reagents, Procedures, and Some Applications). Agriculture Handbook No. 379, Agricultural Research Service, US Department of Agriculture, Washington, D.C.

Hack, P. J. F. M., and S. H. J. Vellinga. 1995. Process for biological treatment of organic material. 1995. U.S. Pat. No. 5,431,819 (Jul. 11, 1995).

Holtzapple, M. T., R. R. Davison, M. K. Ross, S. Aldrett-Lee, M. Nagwani, C.-M. Lee, C. Lee, S. Adelson, W. Kaar, D. Gaskin, H. Shirage, N.-S. Chang, V. S. Chang, and M. E. Loescher. 1999. Biomass conversion to mixed alcohol fuel's using the MixAlco process. Appl. Biochem. Biotechnol. 77-79:609-631.

Hungate, R. E. 1950. The anaerobic mesophilic cellulolytic bacteria. Bacteriol. Rev. 14:1-49.

Hungate, R. E. 1966. The Rumen and Its Microbes. Academic Press, New York.

Kenealy, W. R., Y. Cao, and P. J. Weimer. 1995. Production of caproic acid by cocultures of ruminal cellulolytic bacteria and *Clostridium kluyveri* grown on cellulose and ethanol. Appl. Microbiol. Biotechnol. 44: 507-513.

Kenealy, W. R., and D. M. Waselefsky. 1985. Studies on the substrate range of *Clostridium kluyveri*; the use of propanol and succinate. Arch. Microbiol. 141:187-194.

Kleiman, R. 1990. Chemistry of new industrial oilseed crops, p. 196-203. In: Janick, J., and J. E. Simon (eds.). Advances in New Crops. Timber Press, Portland, Oreg.

Lele, S. 2006. Jatropha. Available online at http://www.jatropha.de/Oil-analysis/chemical_analysis_of_jatropha_oi-Satish-Lele.htm Levy, P. F., J. E. Sanderson, E. Ashare, and S. R. deRiel. 1983. Alkane liquid fuels production from biomass. p. 159-188 In: Wise, D. L. (ed.) Liquid Fuel Developments, CRC Press, Boca Raton, Fla.

Lund, H. 2001. Practical problems in electrolysis. p. 223-293 In: Lund, H., and O. Hamerich, Organic Electrochemistry, $4^{th}$ ed., Marcel Dekker, New York.

Lynd, L. R., P. J. Weimer, W. H. Van Zyl, and I. S. Pretorius. 2002. Microbial cellulose utilization: fundamentals and biotechnology. Microbiol. Mol. Biol. Rev. 66: 506-577.

Olmstead, J. 2009. Fueling resistance?: Antibiotics in ethanol production. Institute for Agricultural and Trade Policy, University of Minnesota, St. Paul, Minn., July 2009.

Regalbuto, J. R. 2009. Cellulosic biofuels—Got gasoline? Science 325:822-824.

Seebach, D., A. K. Beck, and A. Studer. 1995. Some effects of lithium salts, of strong bases and of the cosolvent DMPU in peptide chemistry, and elsewhere. p. 1-275 In: Ernst, B., and C. Leumann. Modern Synthetic Methods 1995. Verlag Helvetica Chimica Acta, Basel.

Speight, J. G. 2006. The Chemistry and Technology of Petroleum, 4th Ed. p. 680-681. CRC Press, Taylor & Francis. Group, Boca Raton, Fla., USA.

Torii, S., and H. Tanaka. 2001. Carboxylic acids. p. 499-535 In: Lund, H., and O. Hamerich, Organic Electrochemistry, $4^{th}$ ed., Marcel Dekker, New York.

Weimer, P. J., and S. M. Abrams. 2001. In vitro fermentation of polydextrose by bovine ruminal microorganisms. Anim. Feed Sci. Technol. 93:115-123.

Weimer, P. J., J. M. Lopez-Guisa, and A. D. French. 1990. Effect of cellulose fine structure on the kinetics of its digestion by mixed ruminal microorganisms in vitro. Appl. Environ. Microbiol. 56:2421-2429.

Weimer, P. J., J. B. Russell, and R. E. Muck. 2009. Lessons from the cow: What the rumen fermentation can teach us about consolidated bioprocessing of cellulosic material. Biores, Technol., 100:5323-5331.

Weimer, P. J., Y. Shi, and C. L. Odt. 1991. A segmented gas/liquid delivery system for continuous culture of microorganisms on solid substrates, and its use for growth of *Ruminococcus flavefaciens* on cellulose. Appl. Microbiol. Biotechnol. 36: 178-183.

Zamora, A. 2005. Fats, oils, fatty acids, triglycerides. Available online at http://www.scientificpsychic.com/fitness/fattyacids1.html Zwart, K. B., H. J. Gijzen, P. Cox and G. D. Vogels. 1988. Anaerobic digestion of a cellulosic fraction of domestic refuse by a two-phase rumen-derived process. Biotechnol. Bioeng. 32:719-724.

We claim:

1. A method for producing hydrocarbons and hydrogen comprising:
 a. fermenting a biomass material containing fermentation medium with an inoculum comprising a mixed culture of microorganisms derived from the rumen contents of a rumen-containing animal, and/or an inoculum from said mixed culture maintained by sequential transfer, and incubating under anaerobic conditions and for a sufficient time to produce volatile fatty acids in said medium in a bioreactor;

wherein said inoculum ferments the carbohydrates, proteins, nucleic acids, organic acids, and other phytochemicals found in said biomass material;

and wherein said inoculum produces volatile fatty acid mixtures, instead of methane or ethanol, as the primary fermentation products from said biomass material;

and wherein said biomass material and/or said fermentation medium is augmented with at least one member of the adjuvant group consisting of organic acids, fatty acids or their salts, glycerol, or alcohols, that are added to said volatile fatty acid mixtures or their salts by combining and mixing with said biomass material and/or with said fermentation medium, and that said combining and mixing with said volatile fatty acid mixtures or their salts increases the combinations and variety of the total mixed fatty acids or their salts in said medium, combinations of which may be converted into many different biobased fuels and biobased products;

b. subjecting said mixed fatty acids or their salts to electrolysis under conditions effective to convert said mixed fatty acids or their salts to hydrocarbons and hydrogen;

wherein the composition of said hydrocarbons that are converted from said mixed fatty acids by said electrolysis are determined by the composition of said biomass material, said adjuvant group, said volatile fatty acid mixtures, and said total mixed fatty acids or their salts in said medium.

2. The method of claim 1 wherein said volatile fatty acids comprise C-2 to C-6 straight or branched chain fatty acids or salts thereof.

3. The method of claim 2 wherein said volatile fatty acids comprise acetic acid, propionic acid, butyric acid, isobutyric acid, 2-methyl butyric acid, valeric acid, isovaleric acid, caproic acid, or salts thereof.

4. The method of claim 1 wherein said hydrocarbons comprise alkanes, alkenes, dienes, trienes or mixtures thereof.

5. The method of claim 4 wherein said hydrocarbons comprise methane, ethane, propane, butane, pentane, hexane, heptane, octane, nonane, decane, ethylene, propylene, butene, pentene, or isomers or mixtures thereof.

6. The method of claim 1 wherein said fermenting is conducted without the addition of a significant amount of methane production inhibitors.

7. The method of claim 1 wherein said time is between about 1 to 4 days.

8. The method of claim 7 wherein said time is between 2 to 3 days.

9. The method of claim 1 wherein said biomass comprises a cellulosic biomass.

10. The method of claim 1 wherein said biomass is selected from the group consisting of plants, plant parts, plant materials, agricultural crops and trees, oilseed crops, forages, grasses, aquatic plants, bagasse, corn stover, corn cobs, dried distillers grains, hay, flax straw, oat hulls, wood and wood wastes and residues of wood and wood wastes, sawdust, paper products, paper processing wastes, cardboard, yard or landscape waste, animal wastes, food wastes, animal processing wastes, animal carcasses, spent sausage casings, and municipal wastes.

11. The method of claim 1 wherein said fermentation medium further comprises glycerol, a glycol and/or an alcohol.

12. The method of claim 1 wherein said fermentation medium further comprises one or more C-8 to C-22 fatty acids, and said electrolysis converts said fatty acids or their salts to hydrocarbons and hydrogen.

13. The method of claim 1 wherein said biomass is not subjected to chemical or enzymatic pretreatment prior to said fermenting which pretreatment would be effective to substantially increase the availability of fermentable substrates in the biomass to said microorganisms.

14. The method of claim 1 wherein said mixed culture of microorganisms derived from the rumen contents are produced by adaptation to anaerobic growth in a biomass-containing fermentation medium.

15. The method of claim 1 wherein said inoculum further comprises a supplemental inoculum selected from the group consisting of *Clostridium kluyveri, Butyrvibrio fibrisolvens*, a mixed culture of microorganisms derived from the rumen, sewage sludge, landfills, soil or aquatic environments, a mixed culture of microorganisms derived from the gut of insects, and mixtures thereof.

16. The method of claim 1 further comprising a contacting said medium containing said volatile fatty acids with a second inoculum selected from the group consisting of *Clostridium kluyveri, Butyrvibrio fibrisolvens*, a mixed culture of microorganisms derived from the rumen, sewage sludge, landfills, soil or aquatic environments, a mixed culture of microorganisms derived from the gut of insects, and mixtures thereof, and incubating under anaerobic conditions and for a sufficient time to further increase the production of, or change the molar proportions of, volatile fatty acids in said medium.

17. The method of claim 1 further comprising removing one or more of cells of said microorganisms, lignin-containing residues, or carbonates or other non-carboxylate anions from said medium prior to said electrolysis.

18. The method of claim 17 wherein said cells, lignin-containing residues, or carbonates or other non-carboxylate anions are removed by filtration, flocculation, settling, centrifugation, precipitation or combinations thereof.

19. The method of claim 1 wherein said mixed fatty acids in said medium are subjected to said electrolysis without extraction therefrom.

20. The method of claim 1 wherein said electrolysis is conducted in an aqueous medium.

21. The method of claim 20 wherein said electrolysis is conducted in the absence of a significant amount of non-aqueous solvents for said volatile fatty acids.

22. The method of claim 1 wherein said electrolysis is conducted using carbon or graphite anode electrodes.

23. The method of claim 1 wherein said electrolysis is conducted using carbon or graphite anode and cathode electrodes.

24. The method of claim 1 wherein said conditions of said electrolysis comprise an anode current density above 1 $mA/cm^2$.

25. The method of claim 24 wherein said conditions of said electrolysis comprise a potential of 2 volts DC or higher.

26. The method, of claim 25 wherein said conditions of electrolysis comprise a potential of 3 volts DC or higher.

27. The method of claim 1, further comprising extracting or separating said volatile fatty acids and/or said mixed fatty acids or their salts from said medium prior to said electrolysis and then concentrating said volatile fatty acids and/or said mixed fatty acids or their salts prior to said electrolysis.

28. The method of claim 27 wherein said volatile fatty acids and/or said mixed fatty acids or their salts are further separated into individual volatile fatty acids and/or said mixed fatty acids or their salts prior to electrolysis.

29. The method of claim 1 wherein said electrolysis further produces carbon dioxide, and said method further comprises collecting said hydrocarbons, said hydrogen, and said carbon dioxide from said electrolysis in a gaseous phase, compressing said gaseous hydrocarbons, said hydrogen, and said carbon dioxide in high pressure tanks, and separating said gaseous hydrocarbons, said hydrogen, and said carbon dioxide.

30. The method of claim 1 further comprising adding one or more C-8 to C-22 fatty acids or their salts to said medium prior to said electrolysis.

31. The method of claim 1 wherein said electrolysis comprises an anode and a cathode and said anode is separated from said cathode by a semi-permeable membrane effective to substantially prevent the passage of non-carboxylate anions larger than carboxylate anions of said mixed fatty acids therethrough.

32. The method of claim 1, further comprising removing said volatile fatty acids and/or said mixed fatty acids or their salts from said fermentation medium during said fermenting.

33. The method of claim 32 wherein said volatile fatty acids and/or said mixed fatty acids or their salts are removed by capacitive deionization or a flow-through capacitor.

34. The method of claim 32 wherein said volatile fatty acids and/or said mixed fatty acids or their salts are removed by capacitive deionization comprising positioning an anode and a cathode electrode within said fermentation medium and applying a first voltage which is effective to adsorb and concentrate carboxylate anions of said volatile fatty acids and/or mixed fatty acids at said anode but which first voltage is below the water oxidation voltage.

35. The method of claim 1 wherein said electrolysis comprises an anode and a cathode and said anode comprises a semi-permeable membrane effective to substantially prevent the passage of one or more of non-carboxylate anions larger than carboxylate anions of said volatile fatty acids and/or said mixed fatty acids, lignins, cells, and proteins therethrough.

36. The method of claim 16 wherein said hydrogen produced by the said electrolysis is contacted with said secondary inoculum.

37. A method for producing hydrocarbons and hydrogen comprising:
a. fermenting a biomass material containing fermentation medium with an inoculum comprising a mixed culture of microorganisms derived from the rumen contents of a rumen-containing animal, and/or an inoculum from said mixed culture maintained by sequential transfer, and incubating under anaerobic conditions and for a sufficient time to produce volatile fatty acids in said medium in a bioreactor;
wherein said inoculum ferments the carbohydrates, proteins, nucleic acids, organic acids, and other phytochemicals found in said biomass material;
and wherein said inoculum produces volatile fatty acid mixtures, instead of methane or ethanol, as the primary fermentation products from said biomass material
and wherein said biomass material and/or said fermentation medium is augmented with at least one member of the adjuvant group consisting of organic acids, fatty acids or their salts, glycerol, or alcohols, that are added to said volatile fatty acid mixtures, or their salts, by combining and mixing with said biomass material and/or with said fermentation medium, and that said combining and mixing with said volatile fatty acid mixtures, or their salts, increases the combinations and variety of the total mixed fatty acids or their salts in said medium; combinations of which may be converted into many different biobased fuels and biobased products;
b. subjecting said mixed fatty acids or their salts to electrolysis under conditions effective to convert said mixed fatty acids or their salts to hydrocarbons and hydrogen further comprising concentrating said volatile fatty acids and/or said mixed fatty acids or their salts in said medium prior to said electrolysis; wherein the composition of said hydrocarbons that are converted from said mixed fatty acids by said electrolysis are determined by the composition of said biomass material, said adjuvant group, said volatile fatty acid mixtures, and said total mixed fatty acids or their salts in said medium.

38. A method for producing hydrocarbons and hydrogen comprising:
a. fermenting a biomass material containing fermentation medium with an inoculum comprising a mixed culture of microorganisms derived from the rumen contents of a rumen-containing animal, and/or an inoculum from said mixed culture maintained by sequential transfer, and incubating under anaerobic conditions and for a sufficient time to produce volatile fatty acids in said medium in a bioreactor;
wherein said inoculum ferments the carbohydrates, proteins, nucleic acids, organic acids, and other phytochemicals found in said biomass material;
and wherein said inoculum produces volatile fatty acid mixtures, instead of methane or ethanol, as the primary fermentation products from said biomass material
and wherein said biomass material and/or said fermentation medium is augmented with at least one member of the adjuvant group consisting of organic acids, fatty acids or their salts, glycerol, or alcohols, that are added to said volatile fatty acid mixtures, or their salts, by combining and mixing with said biomass material and/or with said fermentation medium, and that said combining and mixing with said volatile fatty acid mixtures, or their salts, increases the combinations and variety of the total mixed fatty acids or their salts in said medium; combinations of which may be converted into many different biobased fuels and biobased products;
b. subjecting said mixed fatty acids or their salts to electrolysis under conditions effective to convert said mixed fatty acids or their salts to hydrocarbons and hydrogen; further comprising extracting or separating said volatile fatty acids and/or said mixed fatty acids or their salts from said medium prior to said electrolysis; wherein the composition of said hydrocarbons that are converted from said mixed fatty acids by said electrolysis are determined by the composition of said biomass material, said adjuvant group, said volatile fatty acid mixtures, and said total mixed fatty acids or their salts in said medium.

39. The method of claim 38, further comprising extracting or separating said volatile fatty acids and/or said mixed fatty acids or their salts from said medium prior to said electrolysis and then concentrating said said-volatile fatty acids and/or mixed fatty acids or their salts prior to said electrolysis.

40. The method of claim 39, wherein said volatile fatty acids and/or said mixed fatty acids or their salts are further separated into individual volatile fatty acids and/or mixed fatty acids or their salts prior to electrolysis.

41. The method of claim 1 further comprising concentrating said volatile fatty acids and/or said mixed fatty acids or their salts in said medium prior to said electrolysis.

42. The method of claim 1 further comprising extracting or separating said volatile fatty acids and/or said mixed fatty acids or their salts from said medium prior to said electrolysis.

43. The method of claim 1, wherein step (a) produces volatile fatty acids and about 10% methane and 20% carbon dioxide based on the mass of said biomass material.

44. The method of claim 1, wherein step (a) does not require the removal of lignin from said biomass material.

45. The method of claim 1, wherein at least one member of the group consisting of acetic acid, glycerol and an alcohol is added to said biomass material in step (a).

46. The method of claim 1, wherein said electrolysis uses alternating current as waveforms, magnetic fields, or ultrasonic energy to enhance product yields and variability within the electrolytic cell.

47. The method of claim 1 wherein said inoculum further comprises a supplemental inoculum consisting of *Clostridium kluyveri*.

48. The method of claim 45 wherein said inoculum further comprises a supplemental inoculum consisting of *Clostridium kluyveri*.

49. The method of claim 1, wherein said hydrogen produced by said electrolysis is returned to said bioreactor.

50. The method of claim 1, wherein said biomass material contains proteins.

51. The method of claim 50, further comprising concentrating said volatile fatty acids and/or said mixed fatty acids or their salts in said medium prior to said electrolysis.

52. The method of claim 50, further comprising extracting or separating said volatile fatty acids and/or said mixed fatty acids or their salts from said medium prior to said electrolysis.

53. The method of claim 1, wherein said electrolysis includes semi-porous membranes in the electrolytic cell.

54. The method of claim 1, wherein said fermentation is conducted as a batch, fed-batch or continuous process, or a combination, in a single- or multi-stage bioreactor.

55. The method of claim 1, wherein said volatile fatty acids and/or said mixed fatty acids or their salts are removed from said fermentation medium either continuously or periodically during fermentation.

56. The method of claim 55, wherein said volatile fatty acids and/or said mixed fatty acids or their salts are removed from said fermentation medium either continuously or periodically during fermentation by using a capacitive deionization process.

57. The method of claim 56, wherein said capacitive deionization process is performed using a flow-through capacitor.

58. The method of claim 1, wherein said fatty acids or their salts are separated and removed from said medium, and processed separately from said volatile fatty acid mixtures.

59. The method of claim 1, wherein said electrolysis is carried out with at least one member of the group consisting of an aqueous solvent and non-aqueous solvent in said medium, in an amount sufficient to increase solubility of fatty acids or their salts in said medium prior to said electrolysis.

60. The method of claim 58, wherein the said non-aqueous solvent is selected from at least one member of a group consisting of acetic acid, methanol, ethanol, and isopropanol.

61. The method of claim 1, wherein said mixed culture does not comprise naturally isolated or genetically engineered pure cultures.

62. The method of claim 1, wherein said microorganisms in said mixed culture do not reduce or eliminate acetic acid production as a byproduct of said fermenting.

63. The method of claim 1, wherein said fermenting is conducted without sterilization of said biomass material, said bioreactor, or any other components.

64. The method of claim 37, wherein said microorganisms in said mixed culture do not reduce or eliminate acetic acid production as a byproduct of said fermenting.

65. The method of claim 37, wherein said fermenting is conducted without sterilization of said biomass material, said bioreactor, or any other components.

66. The method of claim 38, wherein said microorganisms in said mixed culture do not reduce or eliminate acetic acid production as a byproduct of said fermenting.

67. The method of claim 38, wherein said fermenting is conducted without sterilization of said biomass material, said bioreactor, or any other components.

68. The method of claim 1, wherein said volatile fatty acids and/or said mixed fatty acids are converted to their carboxylate salts by the addition of a base.

69. The method of claim 68, wherein said base is NaOH, KOH, or $Ca(OH)_2$.

70. The method of claim 37, wherein said volatile fatty acids and/or said mixed fatty acids are converted to their carboxylate salts by the addition of a base.

71. The method of claim 70, wherein said base is NaOH, KOH, or $Ca(OH)_2$.

72. The method of claim 38, wherein said volatile fatty acids and/or said mixed fatty acids are converted to their carboxylate salts by the addition of a base.

73. The method of claim 72, wherein said base is NaOH, KOH, or $Ca(OH)_2$.

74. The method of claim 1, wherein said fatty acids are C-8 to C-22 fatty acids.

75. The method of claim 37, wherein said fatty acids are C-8 to C-22 fatty acids.

76. The method of claim 38, wherein said fatty acids are C-8 to C-22 fatty acids.

77. The method of claim 58, wherein said fatty acids are C-8 to C-22 fatty acids.

78. The method of claim 59, wherein said fatty acids are C-8 to C-22 fatty acids.

* * * * *

UNITED STATES PATENT AND TRADEMARK OFFICE
CERTIFICATE OF CORRECTION

PATENT NO. : 9,663,864 B2
APPLICATION NO. : 14/463971
DATED : May 30, 2017
INVENTOR(S) : Anthony B. Kuhry and Paul J. Weimer Page 1 of 1

It is certified that error appears in the above-identified patent and that said Letters Patent is hereby corrected as shown below:

In the Claims

Column 38 Lines 7-10 should be corrected to read:
60. The method of claim 59, wherein the said non-aqueous solvent is selected from at least one member of a group consisting of acetic acid, methanol, ethanol, and isopropanol.

Signed and Sealed this
Thirtieth Day of April, 2019

Andrei Iancu
*Director of the United States Patent and Trademark Office*